United States Patent
Muzet

(10) Patent No.: US 9,820,680 B2
(45) Date of Patent: Nov. 21, 2017

(54) SYSTEM AND METHOD FOR DETERMINING SLEEP AND SLEEP STAGES OF A PERSON

(75) Inventor: Alain Gilles Muzet, Geispolsheim (FR)

(73) Assignee: V-WATCH SA, Geneva (CH)

( * ) Notice: Subject to any disclaimer, the term of this patent is extended or adjusted under 35 U.S.C. 154(b) by 379 days.

(21) Appl. No.: 14/117,690

(22) PCT Filed: May 15, 2012

(86) PCT No.: PCT/EP2012/059074
§ 371 (c)(1),
(2), (4) Date: Nov. 14, 2013

(87) PCT Pub. No.: WO2012/156427
PCT Pub. Date: Nov. 22, 2012

(65) Prior Publication Data
US 2014/0088378 A1    Mar. 27, 2014

(30) Foreign Application Priority Data
May 18, 2011 (EP) .................................. 11166629

(51) Int. Cl.
*A61B 5/0205* (2006.01)
*A61B 5/00* (2006.01)
(Continued)

(52) U.S. Cl.
CPC .......... *A61B 5/1123* (2013.01); *A61B 5/0205* (2013.01); *A61B 5/02125* (2013.01);
(Continued)

(58) Field of Classification Search
CPC ..... A61B 5/0205; A61B 5/11; A61B 5/02405; A61B 5/4809; A61B 5/4812; A61B 5/4815
See application file for complete search history.

(56) References Cited

U.S. PATENT DOCUMENTS

| 4,836,219 A | 6/1989 | Hobson et al. |
| 5,280,791 A | 1/1994 | Lavie |

(Continued)

FOREIGN PATENT DOCUMENTS

| JP | 4-109961 A | 4/1992 |
| JP | 6-294539 A | 10/1994 |

(Continued)

OTHER PUBLICATIONS

Office Action issued in Chinese application No. 201280035419.X dated Feb. 4, 2015, 16 pages.

(Continued)

*Primary Examiner* — William Levicky
(74) *Attorney, Agent, or Firm* — Rothwell, Figg, Ernst & Manbeck, P.C.

(57) ABSTRACT

The present invention relates to a system and method for determining sleep, sleep stage and/or sleep stage transition of a person, including heart rate detecting means configured for detecting a heart rate of the person, movement detecting means configured for detecting a movement of a part of the body of the person, where the detected movement is caused by a skeletal muscle of the body, recording means configured for recording the detected heart rate and the detected movement of the part of the body, heart rate classifying means configured for classifying the recorded heart rate of the person into at least one heart rate class at least one heart rate variability class, movement classifying means configured for classifying the recorded movement into at least one movement class, and determining means configured for determining sleep, a sleep stage, a sleep stage transition and/or a sleep event of the person based at least partially on the at least one heart rate class and the at least one movement class.

15 Claims, 12 Drawing Sheets

(51) Int. Cl.
*A61B 5/024* (2006.01)
*A61B 5/11* (2006.01)
*A61B 5/021* (2006.01)
*A61B 5/145* (2006.01)

(52) U.S. Cl.
CPC ...... *A61B 5/02405* (2013.01); *A61B 5/02438* (2013.01); *A61B 5/11* (2013.01); *A61B 5/4809* (2013.01); *A61B 5/4812* (2013.01); *A61B 5/4815* (2013.01); *A61B 5/4848* (2013.01); *A61B 5/681* (2013.01); *A61B 5/7264* (2013.01); *A61B 5/7282* (2013.01); *A61B 5/14542* (2013.01); *A61B 5/4818* (2013.01); *A61B 5/4866* (2013.01); *A61B 2560/0242* (2013.01); *A61B 2560/0443* (2013.01); *A61B 2562/0219* (2013.01)

(56) References Cited

U.S. PATENT DOCUMENTS

| | | | |
|---|---|---|---|
| 5,846,206 A * | 12/1998 | Bader | A61B 5/18 600/513 |
| 5,902,250 A | 5/1999 | Verrier et al. | |
| 7,351,206 B2 | 4/2008 | Suzuki et al. | |
| 7,621,877 B2 | 11/2009 | Schnall | |
| 8,292,819 B2 | 10/2012 | Kuo et al. | |
| 2004/0087878 A1* | 5/2004 | Krausman | A61B 5/1118 600/587 |
| 2005/0115561 A1 | 6/2005 | Stahmann et al. | |
| 2007/0106183 A1* | 5/2007 | Suzuki | A61B 5/02438 600/595 |
| 2007/0249952 A1 | 10/2007 | Rubin et al. | |
| 2009/0264715 A1* | 10/2009 | Auphan | A61B 5/08 600/301 |
| 2010/0125215 A1* | 5/2010 | Kuo | A61B 5/0006 600/509 |
| 2012/0210513 A1* | 8/2012 | Chestakov | A61B 5/015/421 |
| 2012/0253142 A1* | 10/2012 | Meger | A61B 5/1116 600/301 |

FOREIGN PATENT DOCUMENTS

| | | |
|---|---|---|
| JP | 2002-34955 A | 2/2002 |
| JP | 2002-219116 A | 8/2002 |
| JP | 2007190126 A | 8/2007 |
| JP | 2009297455 A | 12/2009 |
| JP | 2010273752 A | 12/2010 |
| JP | 2011015887 A | 1/2011 |
| RU | 2005 103 835 A | 8/2005 |
| TW | 201019901 A1 | 6/1999 |
| WO | 98/43536 A1 | 10/1998 |
| WO | 2011/055304 A1 | 5/2011 |

OTHER PUBLICATIONS

2nd Office Action issued in Chinese application No. 201280035419.X dated Sep. 21, 2015, 9 pages.
International Search Report in PCT/EP2012/059074 dated Sep. 20, 2012 (3 pgs.).
English language translation of a Notification of Reasons for Refusal dated Mar. 14, 2016 issued in Japanese Patent Application No. 2014-510784, 4 pages.
Iber, C., et al., "The AASM manual for the scoring of sleep and associated events: Rules, terminology and technical specifications," American Academy of Sleep Medicine, 2007, 57 pages.
Office Action dated Oct. 24, 2016, issued in related Japanese application No. 2014-510784, English translation, 6 pages.
Office Action dated Nov. 30, 2016, issued in related Israeli application No. 229317, English translation, 6 pages.
Office Action (and English translation) issued in Russian Patent Application No. 2013156072, 12 pages (Dec. 7, 2016).
Russian Office Action (and English translation) issued in Russian Patent Application No. 2013156072, 9 pages (Apr. 13, 2016).
European Office Action issued in European Patent Application No. 11166629.3, 11 pages (Nov. 2, 2011).
International Preliminary Report on Patentability issued in International Patent Application No. PCT/EP2012/059074, 12 pages (Nov. 28, 2013).
Malaysian Substantive Examination Adverse Report issued in Malaysian Patent Application No. PI 2013702171, 3 pages (Jul. 14, 2017).
Russian Decision to Grant (with English translation) issued in Russian Patent Application No. 2013156072/14(087481), 21 pages (Jul. 31, 2017).
Japanese Office Action (with English translation) issued in Japanese Patent Application No. 2014-510784, 6 pages (Sep. 4, 2017).

* cited by examiner

SYSTEM AND METHOD FOR DETERMINING SLEEP AND SLEEP STAGES OF A PERSON

CROSS REFERENCE TO RELATED APPLICATION

This application is a 35 U.S.C. 371 National Phase Entry Application from PCT/EP2012/059074, filed May 15, 2012, which claims the benefit of European Patent Application No. 11166629.3 filed on May 18, 2011, the disclosure of which is incorporated herein in its entirety by reference.

The present invention relates to systems and methods for determining sleep and/or sleep stages of a person, and in particular to a system and method for determining sleep stage transitions based on a heart rate class and a movement class derived from the heart rate and a movement of the person.

BACKGROUND OF THE INVENTION

A plurality of people faces problems due to sleep abnormalities and sleep disturbances. For example sleep abnormalities or pathologies are numerous and may be as different as narcolepsy, sleepwalking, or abnormal sleep lengths such as insomnia or hypersomnia. Moreover, the sleep of a person may be disturbed by snoring, which is often associated with the obstructive sleep apnoea syndrome, or by environmental factors, such as light or noise. These sleep disturbances are generally marked by the occurrence of sleep events which combine sudden changes of physiological variables such as autonomic (respiratory or cardiac) or motor modifications. The sleep events can also be caused by symptoms of sleep pathologies such as sleep apnoea, restless leg, abnormal movement, sleepwalking, erratic heart rate, nightmare, night terror, etc. Thus, a snoring sleeper or talking and screaming during nightmare or night terror will usually cause an abnormal sleep event. The consequences of abnormal or disturbed sleep are numerous from a health (care) but also from a social-economic point of view.

In order to detect the reasons of the peoples' sleep abnormalities and disturbances, sleep laboratories can conduct a sleep scoring of the person, i.e. the determination of sleep stages and their transitions. In a sleep laboratory, physiological parameters are observed and corresponding data recorded in a polysomnography. This recording during a polysomnography includes primary data such as electroencephalograms (EEG), electrooculogram (EOG) and electromyogram (EMG), and secondary data such as heart rate, respiration, oximetry and body movements. EEG is used to detect and name brainwaves according to their frequency and amplitude. With an EOG the movement of the eye balls is recognized and analysed. EMG allows for evaluating and recording the electrical activity produced by skeletal muscles.

Classically, sleep scoring is based on the analysis of EEG, EOG and EMG recordings made continuously throughout the sleep period. These physiological data are represented by fluctuations of electrical potentials recorded by small electrodes attached to different parts of the scalp and the face of the tested/recorded person.

Those electrical potentials are then interpreted by a sleep specialist according to internationally accepted rules which define the different stages of sleep. Each sleep stage is characterized by the presence and the abundance of specific EEG waves on the recording. Further, eye movements detected by the EOG recording are mainly present during the Rapid Eye Movement (REM) sleep stage, while EMG shows variations in both its tonic and phasic levels depending on the sleep stage and the simultaneous presence of body movements.

A polysomnography provides various disadvantages. For instance, during an EEG electric potentials are recorded by using electrodes fixed on several sides of the skull, e.g. the electrodes are glued to the face and on the skull.

Also, EOGs and EMGs require the attaching of electrodes and sensors to the face, skull or other body parts of the tested person. To detect eye movement during sleep, an EOG requires electrodes glued or otherwise attached near the eye or on the eyelid of the person.

All these electrodes further require wires that are attached to the electrodes and lead to a device placed near the head of the bed limiting the movement freedom of the tested person. Such recording is therefore obtrusive due to wiring, unusual sleep environments and imposed schedule at bedding conditions. The results of such tests may therefore be distorted due to the changed environment of the tested person.

In addition, polysomnographies provide limitations due to the complexity of the recording techniques. In detail, specific recording places such as sleep laboratories and special equipment as well as well trained staff are necessary. Therefore, polysomnography remains an exceptional and expensive method for sleep evaluation.

A polysomnography system based on detection of eyelid movement (EOG), head movement and a heart beat signal (electrocardiogram—ECG) is described in U.S. Pat. No. 5,902,250. The described system, however, is expensive and creates sleep disturbances due to the amount of sensors and wires necessary. In addition, the system described in U.S. Pat. No. 5,902,250 is not very precise in determining sleep stages and does not determine sleep stage transitions.

Further, U.S. Pat. No. 7,351,206 relates to a sleep state determining apparatus that determines a sleep state based on a series of pulse interval data. Body movement data is determined to remove pulse interval data from the series of pulse interval data that was measured in parallel with the body movement data, if a fluctuation amount of the body movement data is greater than a predetermined threshold. The lacking data lead to imprecise sleep stage determination if the body movements are numerous or of long duration. Thus, the derived results may not be sufficient to reliably score sleep stages.

WO 98/43536 A1 discloses a method for determining the sleep state of a patient. The method includes monitoring the heart rate variability of the patient, and determining the sleep state based on the heart rate variability. The method also may include monitoring the frequency of eyelid movements, and making the sleep state determination based also on the frequency of eyelid movements. A method for determining respiratory pattern includes monitoring heart rate variability by receiving heart beat signals, and determining respiratory pattern from the strength of the signals. A home-based, wearable, self-contained system determines sleep-state, respiratory pattern, assesses cardiorespiratory risk, of a patient based on the frequency of eyelid movements, the frequency of head movements, and heart rate variability.

US 2007/0106183 A1 discloses a sleep state measuring apparatus with an autonomic nerve index obtaining unit that obtains a user's autonomic nerve index; and a sleep periodicity index calculating unit that calculates a sleep periodicity index based on a temporal change of the autonomic nerve index and a change in a user's sleeping cycle, wherein the sleep periodicity index indicates whether the user is sleeping or not according to a user's ideal sleeping cycle as an index, or a dominance index calculating unit that calculates a parasympathetic nerve dominance index which shows dominance of a parasympathetic nerve index included in the autonomic nerve index with respect to a sympathetic nerve index included in the autonomic nerve index for a user during sleep.

US 2009/0264715 A1 discloses a sleep system having sensors capable of gathering sleep data from a person and environmental data during a sleep by the person. A processor executes instructions that analyze this data and control the sleep of the person and the environment surrounding the person. Typically, the instructions are loaded in a memory where they execute to generate an objective measure of sleep quality from the sleep data from the person and gather environmental data during the sleep by the person. Upon execution, the instructions receive a subjective measure of sleep quality from the person after the sleep, create a sleep quality index from the objective measure of sleep quality and subjective measure of sleep quality, correlate the sleep quality index and a current sleep system settings with a historical sleep quality index and corresponding historical sleep system settings. The instructions then may modify the current set of sleep system settings depending on the correlation between the sleep quality index and the historic sleep quality index. These sleep system settings control and potentially change one or more different elements of an environment associated with the sleep system.

US 2010/0125215 A1 discloses a sleep analysis system and a method for analysis thereof. The sleep analysis system includes an analysis device and a sleep sensing apparatus. The sleep sensing apparatus includes an ECG signal collector, a multi-axial accelerometer, a wireless transmitting unit, and a control unit. The ECG signal collector is used for collecting an ECG signal associated with a subject. The multi-axial accelerometer is used for detecting a multi-axial accelerometer signal associated with the subject. The control unit controls the wireless transmitting unit to transmit the ECG signal and the multi-axial accelerometer signal to the analysis device for analyzing sleep of the subject. No distinction is made between stages of Non-REM sleep.

However, due to large uncertainties in determining sleep stages and/or sleep stage transitions compared to classical visual sleep scoring, the percent agreement between these sleep scoring approaches with the classical visual sleep scoring approach is considered as too low by the sleep researchers and sleep clinicians. Therefore, these techniques are not in use yet in the medical world.

It is an object of the invention to provide a system and method for determining sleep states and/or sleep stages and/or sleep stage transitions which reduces the disturbance of the sleep of the tested person and provides reliable results while being sufficiently precise and inexpensive.

This object is solved by the present invention as defined by the independent claims. Preferred embodiments are defined by the dependent claims.

Heart rate variability and a LF/HF ratio of a low-frequency (LF) to a high-frequency (HF) component of heart rate variability (HRV) signal may be used to determine sleep state and the sleep stages. Non transient (stationary) fluctuations in heart rate allow a differentiation of the sympathetic and parasympathetic activation, which are related to a low-frequency (LF) and a high-frequency (HF) component of a heart rate variability (HRV) signal. The resulting LF/HF ratio is a quantitative index of the sympatho-vagal balance and can be computed by means of spectral analysis. The more synchronized the sleep is, the more the LF/HF ratio decreases, whereas the LF/HF ratio is significantly increased during REM sleep, indicating a sympathetic predominance during this period. Thus, spectral analysis of the HRV provides additional information of the ultradian rhythmic behaviour of the autonomic nervous system function beyond the traditional cardiovascular measurements (mean heart rate, blood pressure, etc.).

A disadvantage of this spectral analysis approach is that this ratio must be calculated when the heart rate signal is stationary. When the person is moving, the calculation of this ratio is polluted by the changes in heart rate induced by the movements. In other words the LF/HF ratio can only be used when the person remains still.

Scoring sleep is based not only on the determination of a particular sleep stage but also on determining transitions from one stage to another stage. Determining a sleep state, a sleep stage and/or a sleep stage transition using the LF/HF ratio, in particular determining the exact time of the sleep stage and/or the transition from a sleep stage to another sleep stage is highly problematic and the uncertainty in the determination of the sleep stage and/or the stage transition might be of a few to several minutes when the heart rate is not stationary enough.

For example, there may be slow transitions of the LF/HF ratio, with the LF/HF ratio fluctuating like a sine wave from high to low values and reverse. However, if there is no information on the value of the LF/HF ratio indicating a transition between the sleep stages, transitions from Non-REM to REM sleep stages might be arbitrarily fixed by a horizontal line cutting this fluctuating curve. However, using such a technique, the time of the transition can not be determined precisely enough compared to classical visual sleep scoring and therefore the accuracy of sleep stage determination is not sufficient.

An embodiment of the present invention uses heart rate and body movements to determine a sleep state, a sleep stage and/or a sleep stage transition. In a preferred embodiment, determining a sleep stage and/or sleep stage transition is based on heart rate and body movement classes. For example, a sleep stage transition can be precisely determined by looking simultaneously at the level and the suddenly occurring changes in heart rate and the possible concomitant body movements. If no sign of transition is observed, the person remains in the same state (awake or asleep) or in the same sleep stage in the latter case. In doing so, embodiments of the present invention are not dependent on any stationarity of the heart rate signals and by using their sudden modifications, a transition from one stage to another stage can be determined with an uncertainty of a few seconds.

In accordance with a preferred embodiment, the present invention relates to a system for determining sleep, a sleep stage and/or a sleep stage transition of a person. The system includes heart rate detecting means configured for detecting a heart rate of the person and movement detecting means configured for detecting a movement of a part of the body of the person. The detected movement is caused by a skeletal muscle of the body. The system further includes recording means configured for recording the detected heart rate and the detected movement of the part of the body, heart rate classifying means configured for classifying the recorded heart rate of the person into at least one heart rate class and movement classifying means configured for classifying the recorded movement into at least one movement class. The system also includes determining means configured for determining sleep, a sleep stage and/or a sleep stage transition and/or a sleep event of the person based at least partially on the at least one heart rate class and the at least one movement class.

According to an aspect of this embodiment, the system includes heart rate calculating means configured for calculating a heart rate average, a variability value (including the classically used spectral LF/HF ratio), a rhythm characteristic and/or a heart rate event or change from the recorded heart rate. The heart rate classifying means are configured for classifying the heart rate of the person based on the calculated heart rate average, variability value, rhythm characteristic and/or heart rate event or change.

In a further aspect of the embodiment, the determining means are configured for identifying a specific combination of a heart rate class and a movement class within a specific time period, and the determining means are configured for determining sleep, a sleep stage, sleep stage transition and/or a sleep event based on the identified specific combination.

With respect to an aspect of this embodiment, the movement detecting means comprise movement sensing means configured for sensing an acceleration of a part of the body of the person, where the recording means are further configured for recording the sensed acceleration. The system includes movement calculating means configured for calculating, based on values of the recorded acceleration, at least an intensity and/or a duration of each movement of the part of the body of the person.

According to a further aspect of the embodiment, the movement classifying means are configured for classifying each movement of the part of the body at least into a large movement (LM), a small movement (SM) or a twitch (TM), based on the calculated intensity and/or duration of each movement, and/or configured for classifying each LM, SM and/or TM at least into frequency classes and/or duration classes.

In accordance with another aspect of this embodiment, the system further includes environmental sensing means configured for sensing at least one environmental factor, where the recording means are further configured for recording the sensed at least one environmental factor, and environmental classifying means configured for classifying at least some values of the at least one recorded environmental factor into at least one environmental class. The determining means are further configured for determining sleep, a sleep stage, a sleep stage transition and/or a sleep event of the person based at least partially on the at least one environmental class.

According to an aspect of this embodiment, the environmental sensing means are configured for sensing a noise level, an ambient temperature and/or an ambient light.

In accordance with yet another aspect of the embodiment, the system further includes environmental calculating means configured for calculating at least one average noise level and/or noise event based on the recorded noise level, and/or calculating at least one average ambient temperature level and/or change and/or variation based on the recorded ambient temperature, and/or calculating at least one ambient light level and/or change and/or variation of ambient light level based on the recorded ambient light.

With respect to another aspect of this embodiment, the determining means are further configured for determining a transition from waking to sleeping and/or a transition from one sleep stage to another and/or a transition from sleeping to waking and/or a direct causal effect of at least one recorded environmental factor on a sleep stage transition or a transition from sleeping to waking.

In accordance with an aspect of the embodiment, the system further includes evaluating means configured for evaluating a sleeping or waking state of the person based on the at least one heart rate class, the at least one movement class, the at least one environmental class and/or any combination thereof.

According to a further embodiment, a system for determining sleep, a sleep stage and/or a sleep stage transition of a person comprises a heart rate detecting means configured for detecting a heart rate of the person, and a movement detecting means configured for detecting a movement of a part of the body of the person, wherein the movement is caused by a skeletal muscle of the body. The system further comprises a recording means configured for recording the detected heart rate and the detected movement of the part of the body, a heart rate classifying means configured for classifying the recorded heart rate of the person into at least one heart rate class and at least one heart rate variability class, and a movement classifying means configured for classifying the recorded movement into at least one movement class. The system further comprises determining means configured for determining sleep, a sleep stage, a sleep stage transition and/or a sleep event of the person based at least partially on the at least one heart rate class, the at least one heart rate variability class, and the at least one movement class, wherein the determining means are configured for identifying a combination of a heart rate class, a heart rate variability class, and a movement class within a time interval, and for determining sleep, a sleep stage and/or a sleep stage transition based on the identified combination.

According to a preferred embodiment, the at least one heart rate class comprises a heart rate average class.

In a preferred embodiment, heart rate average classification is based on a heart rate average, with the heart rate average being averaged over a predetermined time interval. Preferably, the predetermined time interval for averaging the heart rate varies depending on a detected body movement on the person. For example, in a preferred embodiment, the heart rate average is calculated by averaging the heart rate over a first time interval if there is some body movement, and is calculated by averaging the heart rate over a second time interval if there are no or few body movements, with the second time interval being longer than the first time interval.

According to a further embodiment, a system for determining sleep, a sleep stage and/or a sleep stage transition of a person includes a wearable device configured for detecting and recording a heart rate of the person and configured for detecting and recording a movement of a part of the body of the person, where the movement is caused by a skeletal muscle of the body, and an analysis device configured for classifying the recorded heart rate of the person into at least one heart rate class, configured for classifying the recorded movement into at least one movement class, and configured for determining sleep, a sleep stage, a sleep stage transition and/or a sleep event of the person based at least partially on the at least one heart rate class and the at least one movement class. The system also includes a data connection configured for communicating data representing the recorded heart rate and recorded movement from the wearable recording device to the analysis device.

In accordance with yet another embodiment, a method for determining sleep, a sleep stage and/or a sleep stage transition and/or a sleep event of a person comprises the steps of detecting a heart rate of the person, recording the detected heart rate, detecting a movement of a part of the body of the person, where the movement is caused by a skeletal muscle of the body, recording the detected movement, classifying the recorded heart rate of the person into at least one heart rate class, classifying the recorded movement into at least one movement class, determining sleep, a sleep stage and/or a sleep stage transition and/or a sleep event of the person based at least partially on the at least one heart rate class and the at least one movement class.

According to an aspect of this embodiment, the method comprises identifying a specific combination of a heart rate class and a movement class within a specific time period, where determining comprises determining the sleep stage based on the identified specific combination.

With respect to another aspect of the embodiment, the method comprises sensing at least one environmental factor, recording the sensed at least one environmental factor, classifying at least some values of the at least one recorded environmental factor into at least one environmental class, and determining a sleep event of the person based at least partially on the at least one environmental class.

According to an aspect of the embodiment, the method includes evaluating a sleeping or waking state of the person based on the at least one heart rate class, the at least one movement class, the at least one environmental class and/or any combination thereof.

In accordance with yet another aspect of the embodiment, the method comprises determining a direct causal effect of at least one recorded environmental factor on a sleep stage transition or a sleep event or a transition from sleeping to waking based at least partially on the at least one environmental class.

Regarding a further embodiment, a system for determining sleep, a sleep stage and/or sleep stage transition of a person includes heart rate detecting means configured for detecting a heart rate of the person, movement detecting means configured for detecting a movement of a part of the body of the person, where the movement is caused by a skeletal muscle of the body, heart rate classifying means configured for classifying the detected heart rate of the person into at least one heart rate class, movement classifying means configured for classifying the detected movement into at least one movement class, and determining means configured for determining sleep, sleep stage and/or a sleep stage transition of the person based at least partially on the at least one heart rate class and the at least one movement class.

With respect to an aspect of this embodiment, the system includes heart rate calculating means configured for calculating a heart rate average, a variability value (including the spectral LF/HF ratio), a rhythm characteristic and/or a heart rate event or change from the detected heart rate, where the heart rate classifying means are configured for classifying the heart rate of the person based on the calculated heart rate average, variability value, rhythm characteristic and/or heart rate event or change.

In accordance with another aspect of the embodiment, the determining means are further configured for identifying a specific combination of a heart rate class and a movement class within a specific time period, where the determining means are configured for determining sleep, the sleep stage and/or the sleep stage transition and/or a sleep event based on the identified specific combination.

In accordance with yet another aspect of the embodiment, the determining means are configured for identifying a successive order of the heart rate class and the movement class of the specific combination.

Regarding another aspect of the embodiment, the determining means are configured for identifying, as a specific combination, a heart rate acceleration event together with a movement of the part of the body, a heart rate acceleration event preceding a movement of the part of the body, a heart rate acceleration event without a movement of the part of the body within the specific time period, and/or a heart rate acceleration event after a movement of the part of the body.

According to another aspect of the embodiment, the heart rate detecting means comprise pulse wave sensing means configured for sensing a pulse wave of the heart of the person.

In accordance with a further aspect of the embodiment, the movement detecting means comprise movement sensing means configured for sensing an acceleration of the part of the body of the person, where the system includes movement calculating means configured for calculating, based on values of the sensed acceleration, at least an intensity and/or a duration of each movement of the part of the body of the person.

In accordance with another aspect of the embodiment, the movement classifying means are configured for classifying each movement of the part of the body into at least a large movement, a small movement or a twitch, based on the calculated intensity and/or duration of each movement.

In accordance with yet another aspect of the embodiment, the movement classifying means are configured for classifying each movement of the part of the body at least into a large movement (LM), a small movement (SM) or a twitch (TM), based on the calculated intensity and/or duration of each movement, and/or configured for classifying each LM, SM and/or TM at least into frequency classes and/or duration classes.

According to another aspect of the embodiment, the system further includes environmental sensing means configured for sensing at least one environmental factor, and environmental classifying means configured for classifying at least some values of the at least one sensed environmental factor into at least one environmental class.

According to yet another aspect of the embodiment, the determining means are further configured for determining a sleep event of the person based at least partially on the at least one environmental class.

Regarding a further aspect of the embodiment, the environmental sensing means are configured for sensing a noise level, an ambient temperature and/or an ambient light.

With respect to yet a further aspect of the embodiment, the system further includes environmental calculating means configured for calculating at least one average noise level and/or noise event based on the sensed noise level, and/or calculating at least one average ambient temperature level and/or a change and/or variation of the sensed ambient temperature, and/or calculating at least one ambient light level and/or change of ambient light level based on the sensed ambient light.

According to another aspect of the embodiment, the determining means are further configured for determining a transition from one sleep stage to another and/or from a sleep stage to wake and/or a sleep event.

According to yet another aspect of the embodiment, the determining means are configured for determining that the transition is a descending transition or an ascending transition, where a descending transition starts from waking or from a lighter sleep stage and leads to a deeper sleep stage, and wherein an ascending transition starts from a deeper sleep stage and leads to a lighter sleep stage or to waking.

In accordance with an aspect of the embodiment, the system further includes identifying means configured for identifying a missing value and/or an abnormal value within the detected heart rate, the detected movement and/or the values of the at least one sensed environmental factor.

Regarding another aspect of the embodiment, the system further includes evaluating means configured for evaluating a sleeping or waking state of the person based on the at least one heart rate class, the at least one movement class, the at least one environmental class and/or any combination thereof.

According to yet another embodiment, a system for determining sleep, a sleep stage and/or a sleep stage transition of a person includes a wearable device configured for detecting a heart rate of the person and configured for detecting a movement of a part of the body of the person, where the movement is caused by a skeletal muscle of the body, an analysis device configured for classifying the detected heart rate of the person into at least one heart rate class, configured for classifying the detected movement into at least one movement class, and configured for determining sleep, a sleep stage and/or a sleep stage transition and/or a sleep event of the person based at least partially on the at least one heart rate class and the at least one movement class, and a data connection configured for communicating data representing the detected heart rate and detected movement from the wearable recording device to the analysis device.

In accordance with an aspect of this embodiment, the identifying means are further configured for recuperating missing data and/or abnormal data.

In accordance with another aspect of the embodiment, the data connection is a wireless data connection.

According to yet another aspect of the embodiment, the wearable device is worn by the person at a limb, the torso and/or the head of the person.

With respect to another aspect of the embodiment, the wearable device is further configured for recording data representing at least successive heart rate intervals, and is configured for recording data representing the detected movement, where the data connection is configured for communicating the recorded data representing at least successive heart rate intervals and/or data representing the detected movement from the wearable device to the analysis device.

Regarding another aspect of the embodiment, the analysis device is further configured for evaluating a sleeping or waking state of the person based on the at least one heart rate class, the at least one movement class and/or any combination thereof.

According to a further embodiment, a method for determining sleep, the sleep stage and/or a sleep stage transition of a person comprises the steps of detecting a heart rate of the person, detecting a movement of a part of the body of the person, where the movement is caused by a skeletal muscle of the body, classifying the detected heart rate of the person into at least one heart rate class, classifying the detected movement into at least one movement class, and determining sleep, a sleep stage and/or a sleep stage transition and/or a sleep event of the person based at least partially on the at least one heart rate class and the at least one movement class.

In accordance with an aspect of this embodiment, the method comprises the step of identifying a specific combination of a heart rate class and a movement class within a specific time period, where determining comprises determining sleep, the sleep stage and/or a sleep stage transition and/or a sleep event based on the identified specific combination.

In accordance with another aspect of the embodiment, the method comprises calculating a heart rate average, a variability value, a rhythm characteristic and/or a heart rate event or change from the detected heart rate, where classifying the heart rate of the person comprises classifying the heart rate based on the calculated heart rate average, variability value, rhythm characteristic and/or heart rate event or change.

According to another aspect of the embodiment, the method comprises the steps of sensing at least one environmental factor and classifying at least some values of the at least one sensed environmental factor into at least one environmental class.

Regarding a further aspect of the embodiment, determining comprises determining a sleep event of the person based at least partially on the at least one environmental class.

According to yet another aspect of the embodiment, sensing the at least one environmental factor comprises sensing a noise level, an ambient temperature and/or an ambient light.

According to an aspect of the embodiment, the method includes evaluating a sleeping or waking state of the person based on the at least one heart rate class, the at least one movement class, the at least one environmental class and/or any combination thereof.

In accordance with a further embodiment, the present invention relates to a system for determining sleep, a sleep stage and/or a sleep stage transition of a person. The system includes a heart rate detector configured for detecting a heart rate of the person and movement detector configured for detecting a movement of a part of the body of the person, where the detected movement is caused by a skeletal muscle of the body. The system further includes a recording unit configured for recording the detected heart rate and the detected movement of the part of the body, a heart rate classifying unit configured for classifying the recorded heart rate of the person into at least one heart rate class and a movement classifying unit configured for classifying the recorded movement into at least one movement class. The system also includes a determining unit configured for determining sleep, a sleep stage and/or a sleep stage transition and/or a sleep event of the person based at least partially on the at least one heart rate class and the at least one movement class.

According to an aspect of this embodiment, the system includes a heart rate calculating unit configured for calculating a heart rate average, a variability value, a rhythm characteristic and/or a heart rate event or change from the recorded heart rate. The heart rate classifying unit is configured for classifying the heart rate of the person based on the calculated heart rate average, variability value, rhythm characteristic and/or heart rate event or change.

In a further aspect of the embodiment, the determining unit is configured for identifying a specific combination of a heart rate class and a movement class within a specific time period, and the determining unit is configured for determining sleep, the sleep stage and/or sleep stage transition and/or a sleep event based on the identified specific combination.

With respect to an aspect of this embodiment, the movement detecting unit comprises a movement sensor configured for sensing an acceleration of the part of the body of the person, where the recording unit is further configured for recording the sensed acceleration. The system includes a movement calculating means configured for calculating, based on values of the recorded acceleration, at least an intensity and/or a duration of each movement of the part of the body of the person.

According to a further aspect of the embodiment, the movement classifying means is configured for classifying each movement of the part of the body at least into a large movement (LM), a small movement (SM) or a twitch (TM), based on the calculated intensity and/or duration of each movement, and/or configured for classifying each LM, SM and/or TM at least into frequency classes and/or duration classes.

In accordance with another aspect of this embodiment, the system further includes an environmental sensor configured for sensing at least one environmental factor, where the recording unit is further configured for recording the sensed at least one environmental factor, and an environmental classifying unit configured for classifying at least some values of the at least one recorded environmental factor into at least one environmental class. The determining unit is further configured for determining a sleep event of the person based at least partially on the at least one environmental class.

According to an aspect of this embodiment, the environmental sensor is configured for sensing a noise level, an ambient temperature and/or an ambient light.

In accordance with yet another aspect of the embodiment, the system further includes an environmental calculating unit configured for calculating at least one average noise level and/or noise event based on the recorded noise level, and/or calculating at least one average ambient temperature level and/or change and/or variation based on the recorded ambient temperature, and/or calculating at least one ambient light level and/or change of ambient light level based on the recorded ambient light.

With respect to another aspect of this embodiment, the determining unit is further configured for determining an ascending transition from one sleep stage to another and/or a transition from sleeping to waking and/or a direct causal effect of at least one recorded environmental factor or a sleep event on an ascending sleep stage transition and/or a transition from sleeping to waking.

In accordance with an aspect of the embodiment, the system further includes an evaluating unit configured for evaluating a sleeping or waking state of the person based on the at least one heart rate class, the at least one movement class, the at least one environmental class or any combination thereof.

According to a further embodiment, the present invention provides a method for determining sleep, a sleep stage and/or a sleep stage transition of a person. The method comprises detecting a heart rate of the person, recording the detected heart rate, detecting a movement of a part of the body of the person, wherein the movement is caused by a skeletal muscle of the body, recording the detected movement, classifying the recorded heart rate of the person into at least one heart rate class and at least one heart rate variability class, classifying the recorded movement into at least one movement class; and determining sleep, a sleep stage, a sleep stage transition and/or a sleep event of the person based at least partially on the at least one heart rate class, the at least one heart rate variability class, and the at least one movement class.

According to a preferred embodiment of the method, the at least one heart rate class comprises a heart rate average class and a heart rate average classification.

In a preferred embodiment, heart rate average classification is based on a heart rate average, with the heart rate being averaged over a predetermined time interval. Preferably, the time interval for calculating the heart rate average varies depending on a detected body movement on the person. For example, in a preferred embodiment, the heart rate average is calculated by averaging the heart rate over a first time interval if there is some body movement, and is calculated by averaging the heart rate over a second time interval if there are no or few body movements, with the second time interval being longer than the first time interval.

Aspects of different embodiments of the present invention can be combined unless stated otherwise.

BRIEF DESCRIPTION OF THE DRAWINGS

In order to describe the manner in which the above-recited and other advantages and features can be obtained, a more detailed description of the subject matter briefly described above will be rendered by reference to specific embodiments which are illustrated in the appended drawings. Understanding that these drawings depict only typical embodiments and are not therefore to be considered to be limiting in scope, embodiments will be described and explained with additional specificity and detail through the use of the accompanying drawings in which.

DETAILED DESCRIPTION OF THE INVENTION

The present invention provides a system and method to score the waking and sleeping periods of an individual, based on the ambulatory recording of both heart rate and body motility, and to describe the characteristics and the variations of the ambient physical environment in which this person is living. During the sleep period, the method will allow to automatically score the different stages of sleep in a similar manner and with the same accuracy as the one classically used through polysomnographical recording and visual scoring. Therefore, the present invention can obtain a detailed sleep description and evaluation fully comparable to the usual method in using much simpler and easier recording methodology. Its recordings, made for example on the wrist of a person, will be less subject to electrical artefacts or wiring limitations than the usual polysomnography. In addition, the present invention is totally autonomous and able to record not only the sleep period but all activities of the living person.

As mentioned above, as used in this document a person's vigilance state can basically be defined as wake or sleep. These states alternate and are dependent on each other.

During sleep, several sleep stages can be determined. These sleep stages can be categorized as rapid eye movement (REM) sleep stage and non-REM sleep stages. The REM sleep stage is the one where vivid dreaming occurs. It can be identified by the occurrence of rapid eye movements under closed eyelids, motor atonia and low voltage EEG patterns. The REM sleep stage, also referred to as REM sleep, is also associated with bursts of muscular twitching, irregular breathing, irregular heart rate and increased autonomic activity. Periods of REM sleep are also referred to as paradoxical sleep. Moreover, the sleep of a person can also be scored into non-REM (NREM) stages, which are numbered 1 to 4.

Figure 1:
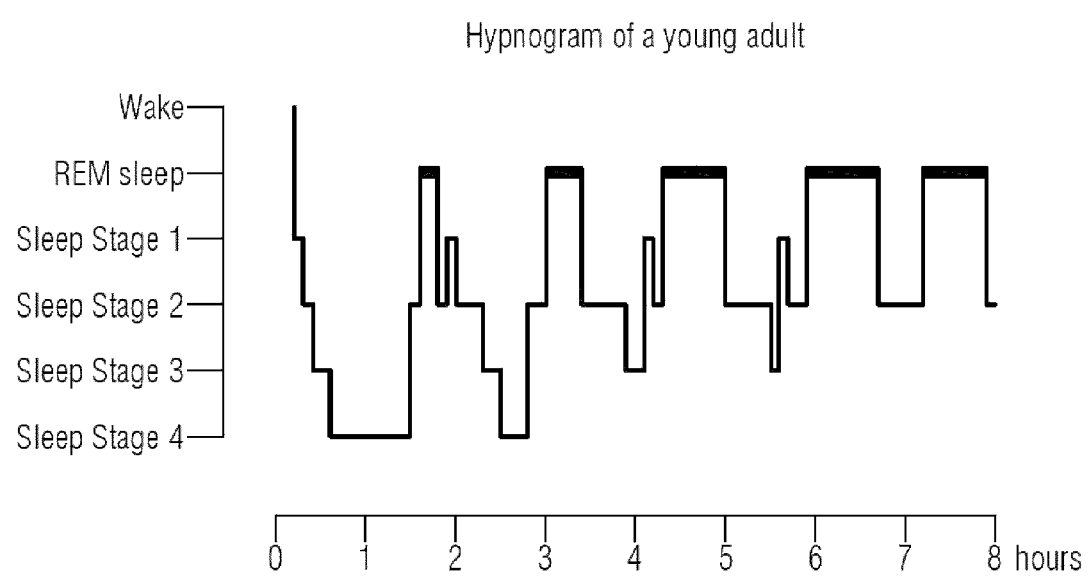
FIG. 1 illustrates a hypnogram of a young adult.

FIG. 1 depicts an exemplary hypnogram of a healthy young adult showing the different sleep stages of an eight hour sleep recording. It must be noted that the transitions from one stage to another are conventionally considered as abrupt steps.

As illustrated, within the first hour of sleep a person starting from a wakeful state and falling asleep may transit to NREM sleep stage 1 and further to stages 2, 3 and 4.

The criteria of sleep stage 1 of the NREM sleep consist of a low voltage EEG tracing with well defined alpha activity and theta frequencies in the 3 to 7 Hz range, occasional vertex spikes, and slow rolling eye movements (SEMs). This stage includes the absence of sleep spindles, K-complexes and REMs. Stage 1 normally represents 4 to 5% of the total amount of sleep time.

The sleep stage 2 of NREM sleep is characterized by the occurrence of sleep spindles and K-complexes against a relatively low voltage, mixed frequency EEG background. High voltage delta waves may comprise up to 20% of stage 2 epochs. The sleep stage 2 usually accounts for 45 to 55% of the total sleep time.

Sleep stage 3 of NREM sleep is defined by at least 20% and not more than 50% of the period consisting of EEG waves of 2 cps or slower, with amplitudes of more than 75 µV (high amplitude delta waves). It is often combined with stage 4 NREM sleep into slow wave sleep (SWS) because of the lack of documented physiological differences between the two stages. This stage 3 normally appears only in the first third of the sleep period of the healthy adult and usually comprises 4 to 6% of the total sleep time.

All above statements concerning NREM sleep stage 3 apply also to sleep stage 4 except that high-voltage, slow EEG delta waves cover 50% or more of the record. NREM sleep stage 4 usually represents 12 to 15% of total sleep time. For instance, sleepwalking, sleep terrors and sleep-related enuresis episodes generally start in stage 4 or during arousal from this stage.

A light Non-REM sleep stage is a common term for the sleep stages 1 and 2, while a deep Non-REM sleep is a term for the combination of sleep stages 3 and 4.

Returning to FIG. 1, after a period of sleep stage 4 the sleep of the tested person changes to sleep stage 2 and to REM sleep. Further, a phase of light Non-REM sleep stages follow to then return to another deep Non-REM sleep stage.

The rest of the sleep as depicted in FIG. 1 comprises transitions from REM sleep periods to lighter Non-REM sleep stages, such as stages 1 and 2.

In order to determine a vigilance state of the tested person and to determine the sleep stages, the sleep stage transitions and/or sleep events of the tested person, the present invention provides a system and method for sensing and recording continuously and up to several days or weeks the basic physiological variables such as heart rate and body motility together with some characteristics of the ambient physical environment. This methodology will be able to score the basic states such as waking and sleeping periods of the tested person. During waking, the present invention will permit to distinguish between active and resting periods. During the sleep state, sleep stages will be scored every 30-second epoch. Moreover, the simultaneous recording of ambient physical variables together with the biological ones will allow evaluating the possible impact of the former to the latter.

Figure 2:
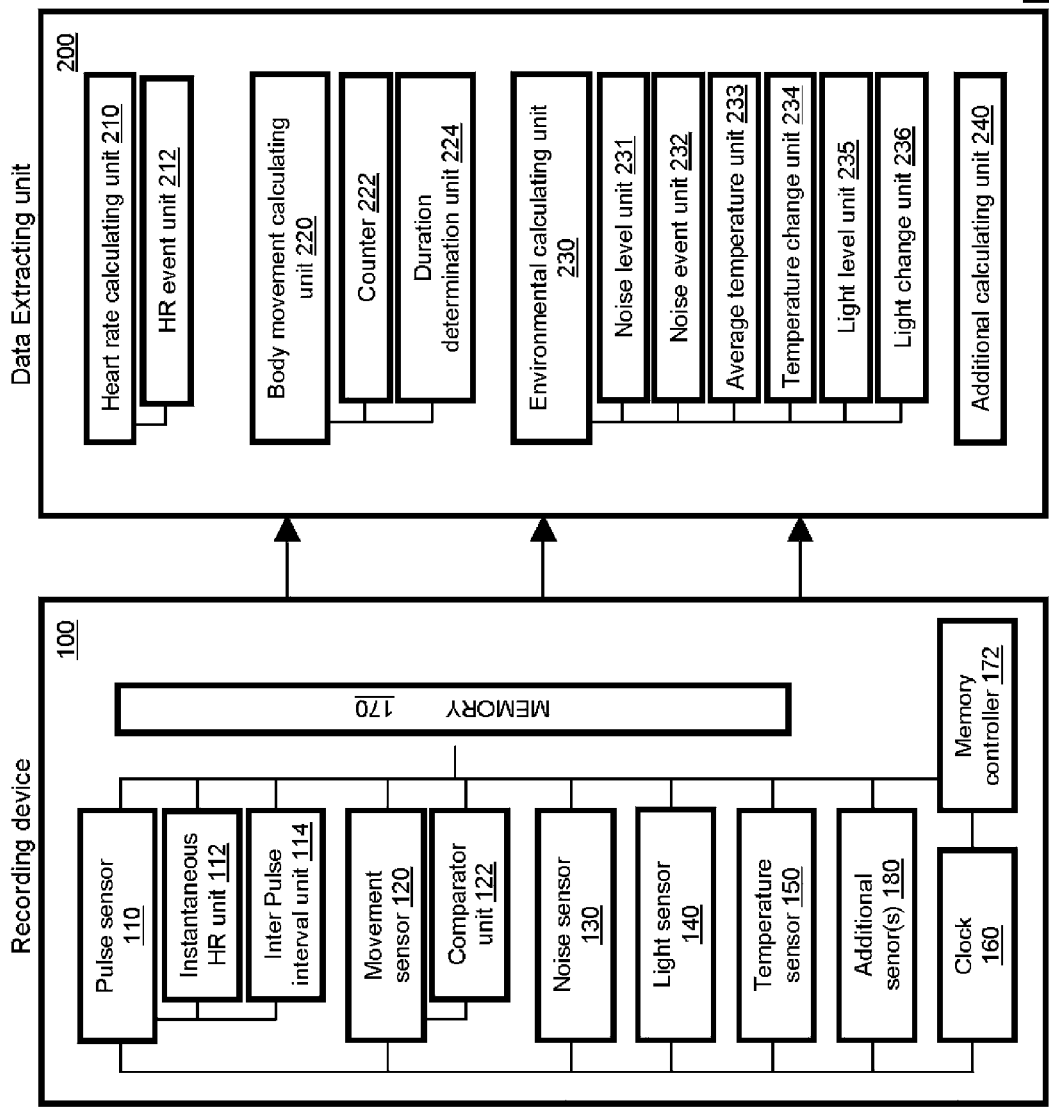
FIG. 2 depicts components of a recording device and a data extracting unit in accordance with an embodiment of the present invention.

FIG. 2 illustrates components of an exemplary sensing/recording system in accordance with an embodiment of the present invention. The present invention is not limited to the depicted arrangement of devices and components. As will be outlined in more detail below, variations of the depicted arrangement are possible and fall also into the scope of the present invention. The exemplary system comprises a recording device 100 that may include detecting means, such as sensors and sensor-related units. Additionally, the recording device 100 includes a memory 170.

The recording device 100 may include a heart rate detecting means that can detect the heart rate of a tested person and output signals representing the heart rate. The heart rate detecting means can be an entity or unit of the recording device 100. Such an entity or unit can be a circuitry, such as an integrated circuit (IC), built to perform the detection of the heart rate and the outputting of the heart rate signals as well as other functions described below. Alternatively, the entity or unit is a circuit capable of running specific software or firmware which performs the functions of the heart rate detecting means as will be outlined in more detail below. Preferably and also alternatively, the entity or unit is a processor, such as a microprocessor, executing a conceptual component of a software or firmware, where execution of the conceptual component performs the below functions of the heart rate detecting means.

For instance, the heart rate detecting means comprise sensors and sensor-related units. These sensors and sensor-related units of the heart rate detecting means may include a pulse sensor 110 sensing a pulse wave of the tested person. The pulse waves can be measured on a peripheral artery. For example, the pulse waves can be measured on a radial artery situated in the wrist, if the recording device 100 is located at the wrist of the tested person. The present invention is not restricted to an artery at the wrist, but the tested person can also wear the recording device at an ankle or other position with access to an artery. The pulse sensor 110 senses the arterial pulse waves produced by the momentary increases of the volume of the arterial vessel due to blood ejected by the heart contractions, i.e. heart systoles. Therefore, these pulse waves correspond exactly to the heart beats.

A sensor-related unit of the heart rate detecting means can be an instantaneous heart rate unit 112 that determines a heart rate (HR) of the tested person based on the sensed pulse wave. The instantaneous HR unit 112 counts the sensed pulse waves for a specified minimum time period and determines a heart rate, i.e. heart beats per minute.

Further, the heart rate detecting means may also comprise an inter-pulse interval unit 114 which measures the elapsed time between two successive pulse waves and outputs the elapsed time, e.g. expressed in milliseconds. This elapsed time is also referred to as pulse wave intervals (PWIs) or heart beat intervals.

Both, the instantaneous heart rate unit 112 and inter-pulse interval unit 114 output data for storage in a memory 170 of the recording device 100 and/or for further calculations. This data represents a heart rate at certain points of time, stored, for example, every second or every 5 seconds. In addition, the data may also represent the elapsed time of at least one PWI as outputted by the inter-pulse interval unit 114. Depending on the memory capacity, the raw sensor data of the sensor 110 can also be recorded and stored in memory 170.

According to another embodiment, the functions of the instantaneous heart rate unit 112 and the inter-pulse interval unit 114 are combined in one unit. Such a combined unit simultaneously outputs an HR value and values representing PWIs for storage in memory 170 or further processing.

Further, according to the depicted embodiment, the apparatus 100 also includes movement detecting means that can detect a movement of the body of the tested person, also referred to as a body movement (BM). The movement detecting means can also be an entity or unit of the recording device 100. As noted above, such an entity or unit can be a circuitry, such as an integrated circuit (IC), built to perform the functions of the movement detecting means described further below. Alternatively, the entity or unit is a circuit capable of running a specific software or firmware which performs these functions. Preferably and also alternatively, the entity or unit is a processor, such as a microprocessor, executing a conceptual component of a software or firmware, where execution of the conceptual component performs the below functions of the movement detecting means.

For scoring the sleep stages or the sleep stage transitions or detecting the sleep events of the tested person, the movement of the skeletal muscles are of primary interest. While eye ball movement and/or a movement caused by the heart and/or lungs of the person may also allow drawing conclusions on the sleep stages, the present invention relies on the movement caused by the skeletal muscles.

The movement detecting means can be a simple sensor 120 allowing determining whether a movement of the sensor occurred. Further, the movement detecting means may also be one or more acceleration sensors 120, which are capable of sensing a body movement more precisely. Such sensing means 120 can be acceleration sensors 120 to sense acceleration along one or more axes. This further allows a determination of a direction, duration and the intensity of a BM.

In a preferred embodiment, the body movement of the tested person will be measured by a miniaturized three-axis accelerometer 120, placed in the recording device 100. The accelerometer 120 measures a value of acceleration for example 20 times per second and all the absolute values are summed for each second. The frequency of measurements and the summing time period may be set in order to adjust the sensitivity of the device 100 to the moving habits of the tested person.

As mentioned above, the recording device can be worn, for example, at the wrist of the tested/recorded person. This is convenient for the person as it does not distract from sleeping as conventional polysomnography instruments and sensors do. Moreover, any movement caused by the skeletal muscles occurs in a part of the body, such as a limb, the torso and/or the head. These movements will in the majority of the cases be accompanied by a slight movement of the wrist.

The sensitivity of the system is therefore chosen in order to detect these movements. The sensitivity of the sensor 120 can be adjusted to personalize the system 100 to the movements of the wearer.

Returning to FIG. 2, the movement detecting means of recording device 100 may also comprise a comparator unit 122 receiving output signals from the sensor 120. The comparator unit 122 compares these output signals with a predefined threshold. Only if acceleration on one or more axes exceeds the predefined threshold, is the particular movement represented by the outputted signal of the sensor 120 recorded, i.e. stored in memory 170. Thus, the sensitivity of the acceleration sensing system can be adjusted by choosing the predefined threshold. Further, the system of the present invention allows for setting a threshold for each axis or for each acceleration sensor 120 of recording device 100. The system can then be adjusted to emphasize particular movements of the wrist, as a movement in the direction along the arm might be less intensive than in a direction orthogonal to the arm.

According to another aspect, the comparator unit 122 holds more than one threshold to which the sensed acceleration is compared. This allows a pre-classification of the movements based on the magnitude of the sensed acceleration.

The output of the sensor 120 is stored in memory 170 for further processing. As mentioned above, the storing may depend on the output signals of the comparator unit 122.

In addition to the above sensors and units the recording device 100 may also include environmental sensing means for sensing an environmental factor. As noted above, the environmental sensing means can also be an entity or unit of the recording device 100. An entity or unit can be a circuitry, such as an integrated circuit (IC), built to perform the functions of the environmental sensing means described below. Alternatively, the entity or unit is a circuit capable of running a specific software or firmware which performs these functions. Preferably and also alternatively, the entity or unit is a processor, such as a microprocessor, executing a conceptual component of a software or firmware, where execution of the conceptual component performs the below functions of the environmental sensing means.

The environmental sensing means may comprise several units, such as a noise sensor 130, a light sensor 140 and/or a temperature sensor 150.

For instance, the ambient physical characteristics of the tested person can be sensed. The noise may be recorded as an integrated value every second and the ambient noise level is measured every second (Leql sec) within a range from 20 to 100 dB with a precision of 1 dB. The ambient light is measured every second in a range of 10 to 1000 lux with a precision of 1 lux. The ambient temperature is measured every second with a dedicated temperature sensor 150 within a range of −20 to +50° C. with a precision of 0.5° C. All ambient physical values are recorded in the internal memory 170 of the device 100.

Returning back to FIG. 2, the recording device 100 may also include additional sensing means 180. As already described above, the additional sensing means 180 can be an entity or unit of the recording device 100. An entity or unit can be a circuitry, such as an integrated circuit (IC), built to perform the functions of additional sensing means described below. Alternatively, the entity or unit is a circuit capable of running a specific software or firmware which performs these functions. Preferably and also alternatively, the entity or unit is a processor, such as a microprocessor, executing a conceptual component of a software or firmware, where execution of the conceptual component performs the below functions of the environmental sensing means.

The additional sensing means 180 can, for example, include physiological sensors made specifically for measuring the blood saturation in oxygen, also referred to as "pulse oximetry". This sensor measures the oxygen saturation in the circulating blood. Its value is normally close to 100% in a healthy sleeper. Desaturation with values below 90% might be observed in sleep apnoea syndrome.

Further additional sensors 180 may be sensors to measure a pulse transit time or sensors measuring the skin temperature or sensors detecting the skin potential variations.

Pulse transit time is directly related to arterial blood pressure. The wall of an artery is elastic and it contains small muscles which can modify the diameter of the vessel. For each contraction of the heart, a certain amount of blood is ejected into the arterial vessels with a certain force. This blood pressure depends on the tension of the arterial wall. If this tension is high, the blood pressure is elevated and if this tension is reduced, the blood pressure is diminished. The speed of the pulse corresponding to a heart beat depends on the rigidity of the wall of the arteries. Therefore, the pulse is accelerated when the tension of the wall is high and diminished when the tension is lower. The transit time is then calculated between two sites placed on the same artery and separated by several centimeters. A same passing pulse is measurable on these two separated sites and the elapsed time is directly related to the tension of the artery wall or the blood pressure. A shortening of this time corresponds to an increase in blood pressure while a lengthening of this elapsed time corresponds to a lowering in blood pressure. The value of this elapsed time is dependent on the distance between the two sites, and the variation of this time gives a value of the variation of the blood pressure, which can be calibrated.

Skin temperature can be measured by a small sensor attached to the skin surface. It gives a good indication of the caloric exchanges between the skin and the environment. Its variations can be indicative of adaptation to changing ambient temperature or of modifications of the vigilance state. It is also possible to measure the variations of the skin electrical potentials by using adequate sensors. This measure is an indirect indicator of sympathetic nervous system activity. It can be indicative of a certain reactivity to the environment or of a particular emotional state, including a possible stress of the person.

According to an embodiment of the present invention, the recording device is separated into at least two modules. One of these modules includes only the above described physiological sensors 110 and 120 and/or the sensor-related units 112, 114 and 122. Such a device is compact and may not exceed the dimensions of, for example, a watch. The second module may include environmental sensors 130, 140 and/or 150. A third module may comprise the additional sensor 180. The additional sensor 180 may also be included in one of the first and second modules if possible.

Such a separation has the advantage that during the night, while the person is in bed, the module devoted to the physiological variables will still be attached to the person while the module devoted to the ambient factors could be separated and placed on the side such as on the bed table. This allows for obtaining more stable environmental values and will avoid noise artefacts due to moving sheets or changes in light level due to a covered or uncovered light sensor depending on the posture of the sleeper.

Each of such separated modules may either include its own memory or only a first module includes a memory while the second and/or third module transmit(s) data from its sensors and sensor-related units to the first module for storage. The transmission of the data may be accomplished by a wireless connection as explained in more detail below.

The at least two separated modules may also be built in such a way as to connect them in order to form a single device. In such a case, the modules include attaching means and electrical connectors in order to function as a single device. For instance, if only one module has a memory, the electrical connectors can be used to transmit data from one module to the memory of the other module.

In any case, a recording device 100 according to each of the above described embodiments may also include a clock 160. The output signal of the clock 160 is transmitted to each of the above described sensors or units 110 to 150 and 180. The sensors 110, 120, 130, 140, 150 and/or 180 and the units 112, 114 and/or 122 may use the outputted clock signal for determining values that depend on time. As an example only, the instantaneous heart rate unit 112 and/or inter-pulse interval unit 114 may use the clock signal to determine the heart rate of the tested person and to measure the elapsed time between two successive pulse waves, respectively.

As mentioned above, the recording device 100 may include recording means for recording the detected heart rate, body movement and/or environmental factor. The recording means can be an entity or unit of the recording device 100. An entity or unit can be a circuitry, such as an integrated circuit (IC), built to perform the functions of the recording means described below. Alternatively, the entity or unit is an IC capable of running a specific software or firmware which performs these functions. Preferably and also alternatively, the entity or unit is a processor, such as a microprocessor, executing a conceptual component of a software or firmware, where execution of the conceptual component performs the below recording functions.

The recording means can comprise a memory 170 which is connected to the above described sensors and units of the recording device 100. The memory 170 may be connected to the sensors and units via a bus and is capable of storing the output signals of the sensors 110, 120, 130, 140, 150 and/or 180 received via the bus.

To correctly store the sensed values, the recording means may further comprise a memory controller 172 which is connected to the bus as well as to the clock 160. Thus, the memory controller 172 can control the storing of the sensed values and may add a time stamp or other signal which will be stored in combination with each sensed value. This allows further evaluations and/or calculations on the sensed values at a later time.

The memory controller 172 may also be in charge of storing the output values of the units 112, 114 and/or 122. The memory controller 172 stores in memory 170 the output values of these units and an optional time stamp or indication of a time period associated with each output value.

According to another embodiment, the device 100 does not include memory 170 and memory controller 172. In this case, only the sensors 110, 120, 130, 140, 150 and/or 180 and associated units 112, 114 and/or 122 would be present in the device 100. The output signals of the sensors and units described above would then be transmitted to a further device for storage and/or further calculations. For example, such a sensing device would continuously transmit sensed values to a device which can receive the data and stores the received sensor values and/or output values of the units described above. The data transmission can, for example, be implemented as a wireless connection (wireless LAN, Bluetooth, infrared data communication) or a wired connection (universal serial bus (USB), Firewire, LAN or other network connection).

In accordance with a further aspect of the present invention, the recording device 100 may include a button or other actuator (not shown). If the tested/recorded person actuates it, e.g. by pressing the button, the recording devices stores the current time together with an indication of the actuation of the button. This allows for marking particular events with a simple push on a button by the person. As an example, only the person could press the button when he or she decides to voluntarily interrupt the recording system, for instance to take a bath, or before going to sleep and once again immediately after waking up in the morning. These marked events can then be used at a later stage of the system to easier identify particular events as will be more apparent from the below description.

The recording device 100 may also have more than one actuator to identify various predefined events. According to another aspect, the actuator may be used in a certain manner to identify different events, such as holding it for 1, 2 or 3 seconds or pressing it once, twice etc.

With respect to all embodiments, the recorded data stored in memory 170 may be employed for further calculations and determinations by a data extracting unit 200. Therefore the data is communicated from memory 170 to data extracting unit 200. A data connection for this data communication may also be implemented as a wireless or wired connection. For instance, a wireless connection may be based on wireless LAN, Bluetooth, infrared data communication or other wireless communication technique. A wired data communication can be implemented with a universal serial bus (USB), Firewire, LAN or other network connection.

According to a further aspect, the data extracting unit 200, including at least some of its below described sub units, and recording device 100 can be integrated into one device. In this case, the data extracting unit 200 may have direct access to memory 170, e.g. via a bus. Such a device can be built, for example, as a wearable device for detecting and recording a heart rate and/or body movement of a person wearing the device. To reduce distraction of the tested person during sleep, the wearable device can be formed similar to a watch that is worn at a wrist of the person. As people are used to wear a watch they will be less distracted by such a device during sleep than by the electrodes and wiring of a polysomnography.

Returning to the embodiment depicted in FIG. 2 and data extracting unit 200, a heart rate calculating means 210 may be part of data extracting unit 200. As already outlined for the means of recording device 100, the heart rate calculating means 210 can also be an entity or unit. An entity or unit can be a circuitry, such as an integrated circuit (IC), built to perform the functions of the heart rate calculating means. Alternatively, the entity or unit is a circuit capable of running a specific software or firmware which performs these functions. Preferably and also alternatively, the entity or unit is a processor, such as a microprocessor, executing a conceptual component of a software or firmware, where execution of the conceptual component performs the below heart rate calculating functions.

The heart rate calculating means 210 evaluates the recorded data from the pulse sensor 110, instantaneous HR unit 112 and/or inter-pulse interval unit 114. For instance, the heart rate calculating means 210 extracts elaborated heart rate data from raw values of the above described successive pulse wave intervals (PWI). The data calculated and outputted by heart rate calculating means 210 may comprise HR averages, HR variability values, rhythm characteristics and/or HR events or changes as will now be explained in more detail.

In detail, HR averages can be of two types: global HR average (GHRA) and resting HR average (RHRA). GHRA will be calculated over rather long periods of time, such as 5 to 10 minutes depending on the time of the day or night. Further, the standard deviation of this average will be used for quantifying the HR variability (HRV) over the considered period. Therefore, GHRA calculation will include periods without any body movement (BM) as well as periods with body movement. It will also give an overall HR average reflecting the influence of ambient factors, such as noise, temperature or light variations. RHRA will be calculated over much shorter periods, for example 10 to 60 seconds depending on the vigilance state, and during periods when no BM is present or was present during the preceding 10 seconds. The standard deviation of this average will be calculated to qualify the HR rhythm, i.e. whether it is regular or irregular. Therefore, RHRA is independent of motor activity of the tested person while it can still be influenced by the environmental factors.

The calculation of a heart rate average, such as the GHRA average or the RHRA average, can be done by averaging the heart rate over a predetermined time interval (time period). The time interval for calculating a heart rate average, e.g. the GHRA average or the RHRA average, can be fixed. For example, the GHRA (which includes periods with and without body movements) can be calculated by averaging heart rate over, e.g. 5 minutes, 10 minutes, etc., and the RHRA can be calculated by averaging the heart rate over, e.g. 5 seconds, 10 seconds, 30 seconds, 60 seconds, etc.

A heart rate average can also be calculated by averaging the heart rate over different predetermined time intervals. Specifically, a heart rate average can be calculated by averaging the heart rate over a first time interval in a first situation, and by averaging the heart rate over a second time interval in a second situation. For example, in a situation with simultaneously occurring body movements, the heart rate average could be calculated by averaging the heart rate over a shorter time interval (e.g. 5 heart beats), whereas in a situation without or with only a few (insignificant) body movements, the heart rate average could be calculated by averaging the heart rate over a longer time interval (e.g. 30 heart beats). The averaging interval could vary in two or more steps (e.g. 2, 3, 4, 5, etc.) or could vary continuously (e.g. inverse to an amount and/or intensity of body movements). If the time interval is varied in steps, threshold values for body movement could be used to select the appropriate time interval for averaging the heart rate. For example, if the amount and/or intensity of body movements falls below a threshold, a longer time interval can be used for averaging the heart rate. The body movement thresholds for selecting different time interval lengths could be defined similar to the body movement classes described further below. The time interval for calculating a heart rate average could also be changed according to a detected body movement class described further below.

Varying the time interval for calculating a heart rate average allows to provide enhanced accuracy and temporal resolution when higher accuracy is needed, e.g. in situations where there are body movements. In this latter case, the average made over a short time interval will still show the variation of the heart rate curve while an average made on a longer time interval would smooth it too much. In situations with no or relatively few (insignificant) body movements, the time interval for averaging can be raised, in order to enhance classification quality, e.g. by reducing the number of erroneously detected sleep stage transitions.

The averaging interval can be determined in terms of heart beats, or can also be determined in terms of seconds and/or minutes. Further, the time interval for calculating a heart rate average could also be depending on the current heart rate and/or heart rate average.

Figure 9:
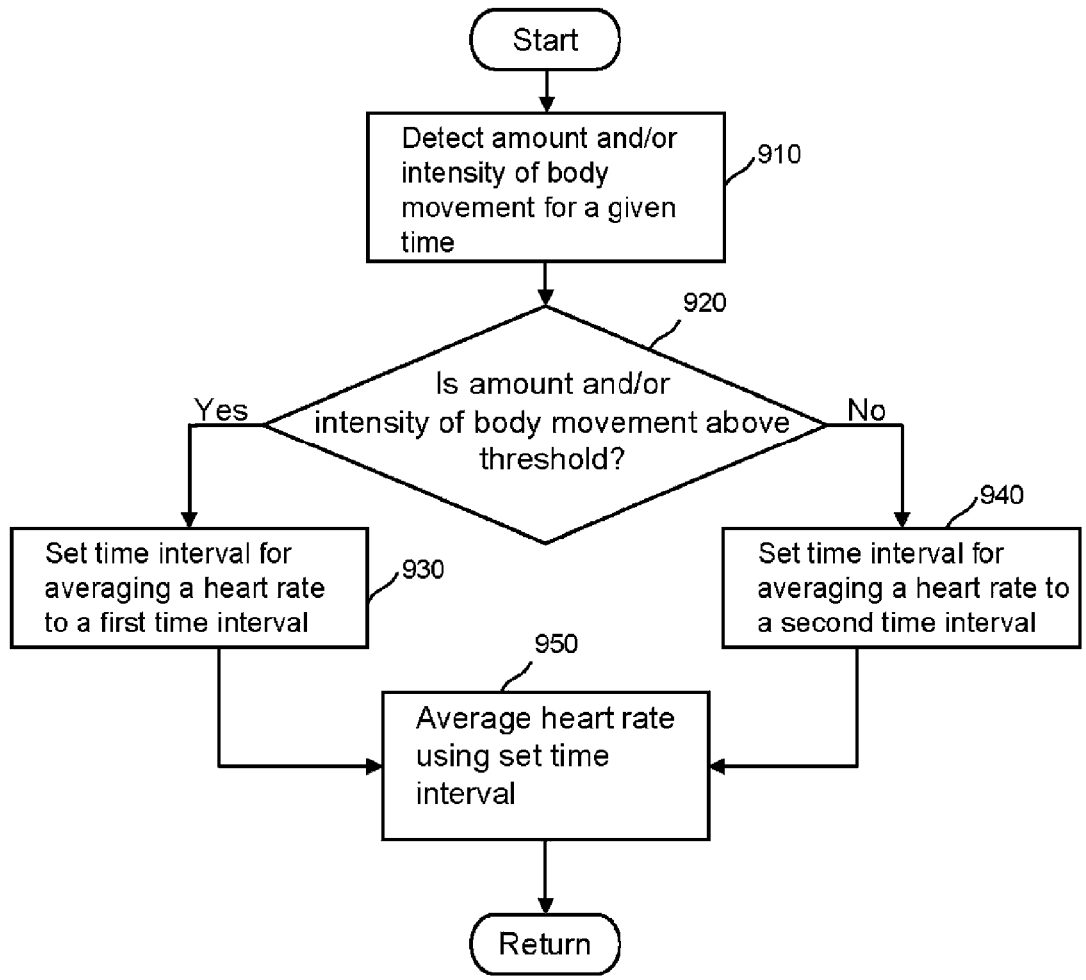
FIG. 9 illustrates method steps for adapting a time interval for averaging a heart rate.

FIG. 9 illustrates an exemplary set of method steps for adapting a time interval for averaging a heart rate. At step 910, an amount and/or intensity of body movement is detected for a given time. The detection could, for example, be carried out in real time, or could be carried out after data has been recorded for several minutes, hours, or days. At step 920, the detected amount/intensity of body movement is compared with a predetermined threshold. The threshold may, for example, be related to thresholds indicating a sleep stage, a sleep stage transition, etc.

If the detected amount/intensity of body movement is higher than the threshold, the method proceeds with step 930. If the detected amount/intensity of body movement is lower than or equal to the threshold, the method proceeds with step 940. At step 930, the time interval for averaging the heart rate is set to a first time interval t1, and at step 940, the time interval for averaging the heart rate is set to a second time interval t2. Preferably, the time interval t2 is longer than the first time interval t1.

The method then proceeds with step 950 and averages the heart rate using the set time interval as determined by step 930 or 940.

The method can then be repeated for another time instant. To do so, the evaluation time could, for example, be shifted by a fixed time, or by a variable time, such as the time interval selected in step 930 or 940. Preferably, the method is repeated until all data samples have been evaluated.

Figure 7:
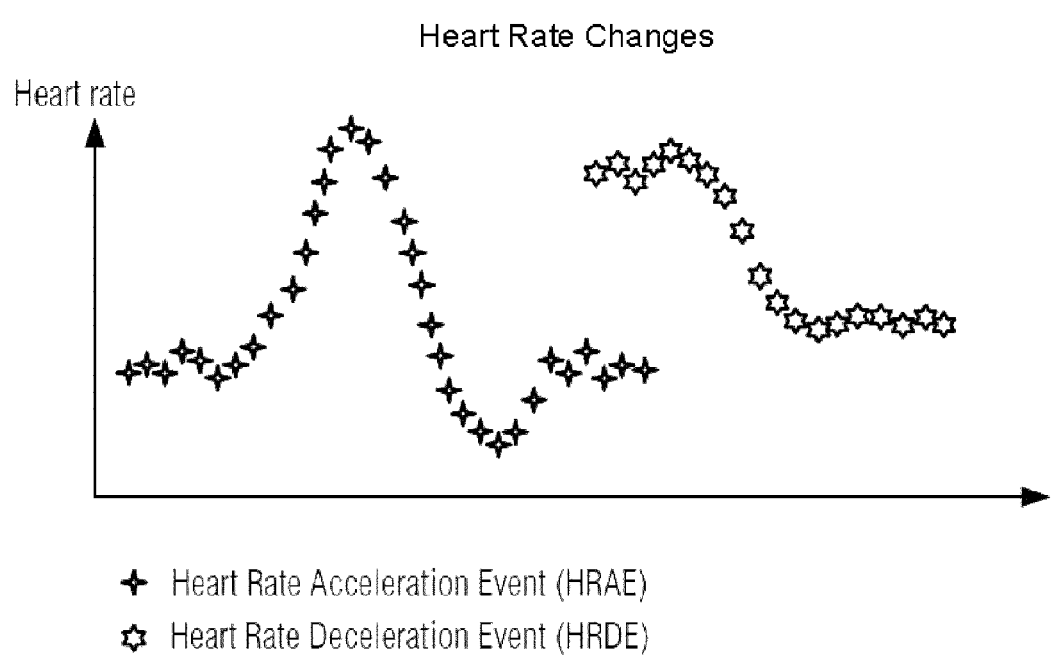
FIG. 7 illustrates heart rate events or changes over time.

Further, returning to FIG. 2, a HR event unit 212 can extract data from memory 170. The HR event unit 212 determines the variation of the interval between two successive pulses which gives a direct value of the variation in heart rate. A reduction of this time interval corresponds to a heart rate acceleration while a lengthening of this interval corresponds to a lower heart rate. Thus, two types of HR changes can be extracted from the data stored in memory 170: HR acceleration (HRA) and HR deceleration (HRD). These changes will last for a few seconds to a few tens of seconds depending of the vigilance state and time of the day. They will be detected in calculating a sliding window average and conducting corresponding analyses made over a few seconds. Exemplary heart rate gradients over time for an HRA and an HRD are depicted in FIG. 7.

In particular, an HRA will be seen when the tested person is moving or when an activation or arousal is occurring. It is a biphasic variation with an initial heart rate acceleration followed by a heart rate deceleration. This deceleration can be accentuated and the lowest HR value can be lower than the initial average level. During wakefulness, any BM or reaction to an external stimulus of the physical environment will be accompanied by an HRA. During sleep, HRA will be produced by any BM or by an arousal. Such an arousal can be internal or due to an external cause, for example noise. HRA will be defined by its amplitude, i.e. the difference between the highest instantaneous HR value and the next lowest instantaneous HR value, and its duration, i.e. from the start of the acceleration to the return of the initial HR value (see also FIG. 7).

Moreover, an HRD will be seen in the absence of any BM or arousal. It is a monophasic change with a progressive diminution of the average heart rate from one level to a lower one. It is generally seen when the subject is relaxing or when there is a transition from waking to light sleep or from light sleep to deep sleep. In these latter cases, HRD can last for several minutes.

In addition, heart rate calculating means 210 can also determine whether some of the pulse wave interval (PWI) data items are abnormal or missing. In order to improve the classification of the HR data, the present invention also provides for recuperation of missing or abnormal pulse wave interval data. The heart rate calculating unit 210 may therefore perform recuperation of PWIs as outlined in more detail below with respect to FIG. 6.

Returning to FIG. 2, data extracting unit 200 may further include a body movement calculating means 220. As noted before, the body movement calculating means 220 can also be an entity or unit. An entity or unit can be a circuitry, such as an integrated circuit (IC), built to perform the functions of the body movement calculating means. Alternatively, the entity or unit is a circuit capable of running a specific software or firmware which performs these functions. Preferably and also alternatively, the entity or unit is a processor, such as a microprocessor, executing a conceptual component of a software or firmware, where execution of the conceptual component performs the below body movement calculating functions.

This body movement calculating means 220 calculates, based on values of the recorded acceleration, the intensity and/or the duration of each body movement of the person. For instance, the body movement calculating means 220 accesses and evaluates the recorded data from the acceleration sensor 120 and the comparator unit 122.

As described above, the recorded raw data of body movements can be obtained in regard to a certain time period. For instance, depending on the processing power and memory capacity, this time period may be adjusted from less than one second to more than five or even ten seconds. Preferably, the recorded raw data of body movement is obtained every second.

A counter 222 may be part of body movement calculating means 220 or may be a separate unit within data extracting unit 200. The counter 222 determines the intensity of the movement by counting the number of BMs per second.

Another unit comprised in or connected to body movement calculating means 220 can be a duration determination unit 224. Unit 224 calculates the duration of the body movement, i.e. the number of successive seconds where movement counts have been determined by counter 222.

According to another embodiment, the counter 222 and/or duration determination unit 224 may also be part of the recording device 100. As recording device 100 provides a clock 160, the acceleration sensed by sensor 120 may be directly used by counter 222 and duration determination unit 224. Further, according to such embodiment, the counter 222 and duration determination unit 224 store their resulting outputs in memory 170.

Returning back to the embodiment depicted in FIG. 2, the data extracting unit 200 may further comprise an environmental calculating means 230 which calculates particular values of the recorded data sensed by the noise sensor 130, light sensor 140 and/or temperature sensor 150. The environmental calculating means 230 can be an entity or unit of data extracting unit 200. Such an entity or unit can be a circuitry, such as an integrated circuit (IC), built to perform the functions of the environmental calculating means 230. Alternatively, the entity or unit is a circuit capable of running a specific software or firmware which performs these functions. Preferably and also alternatively, the entity or unit is a processor, such as a microprocessor, executing a conceptual component of a software or firmware, where execution of the conceptual component performs the below environmental calculating functions.

The environmental calculating means 230 may comprise a noise level unit 231, which determines whether an ambient noise exceeds a predefined level or threshold. Moreover, the noise level unit 231 may also compare the sensed noise values stored in memory 170 with two or more thresholds to determine different levels of noise.

A noise event unit 232 can also be included in environmental calculating means 230 and evaluates from the sensed noise data whether a particular noise event has occurred. A noise event can, for example, be a noise exceeding a particular level over a predefined period of time, such as those levels determined by noise level unit 231.

In addition, environmental calculating means 230 can include an average temperature unit 233 that calculates average values of the ambient temperature over certain periods of time. For instance, the ambient temperature may be averaged over 10 minute intervals, 30 minute intervals or 1 hour intervals. The present invention is not restricted to a particular time period for averaging the ambient noise. Thus, any other time period such as 2, 4 or 6 hours may also be possible.

Moreover, environmental calculating means 230 may also include a temperature change unit 234. The temperature change unit determines whether the temperature has changed between certain points of time. For instance, the temperature change unit 234 may determine whether the temperature has changed by a predefined value of degrees between a point of time and, for example, 5 or 10 minutes later. The temperature change unit 234 may also determine temperature changes over particular periods of time which can be preset. These periods of time may be five minutes, ten minutes, 30 minutes, 60 minutes or longer. The present invention is not restricted to any particular time period but may also be based on other preset time periods.

A light level unit 235 included in environmental calculating means 230 determines whether the light exceeds a particular value based on the recorded light data. The light level unit may comprise a plurality of preset thresholds to which the recorded light data is compared.

Further, the calculating means may comprise a light change unit 236 for determining changes in the values of the recorded light data.

Further, the data extracting unit 200 may further comprise an additional calculating means 240 which calculates particular values of the recorded data sensed by additional sensor(s) 180. The additional calculating means 240 can be an entity or unit of data extracting unit 200. Such an entity or unit can be a circuitry, such as an integrated circuit (IC), built to perform the functions of the environmental calculating means 240. Alternatively, the entity or unit is a circuit capable of running a specific software or firmware which performs these functions. Preferably and also alternatively, the entity or unit is a processor, such as a microprocessor, executing a conceptual component of a software or firmware, where execution of the conceptual component performs the below environmental calculating functions.

The additional calculating means 240 can be adapted to perform any calculations necessary based on the kind of additional sensor(s) 180. For instance, if the additional sensor 180 senses a pulse oximetry, the additional calculating means 240 can calculate one or more levels of blood saturation based on one or more predefined thresholds. In addition, if the additional sensor(s) allow(s) for determination of the pulse transit time (PTT), the additional calculating means 240 conduct the calculation of the PTT, which was already described above.

Further, the additional calculating means 240 can also calculate the caloric exchanges between the skin and the environment based on the sensed skin temperature. Also an activity of the sympathetic nervous system can be determined by the additional calculating means 240 by comparing the sensed electrical potentials of the skin to one or more thresholds. Thus, one or more levels of skin temperature and/or electrical potentials of the skin can be calculated.

The data extracting unit 200 and all its components, such as means or units 210 to 240, will access the recorded data stored in memory 170 of recording device 100. As mentioned above, this data access can be implemented via a bus or a data connection. The output of units 210 to 240 of data extracting unit 200 is also stored in a memory (not shown) of data extracting unit 200 for further determination.

In a further embodiment, the data extracting unit 200 is part of recording device 100. In this case, the units 210 to 240 can use memory 170 for reading recorded data values and for writing calculated output values. With respect to this embodiment, the combined device is capable of transmitting the data extracted by data extracting units 210 to 240 to another device via a wired or wireless interface and data connection as described above.

Figure 3:
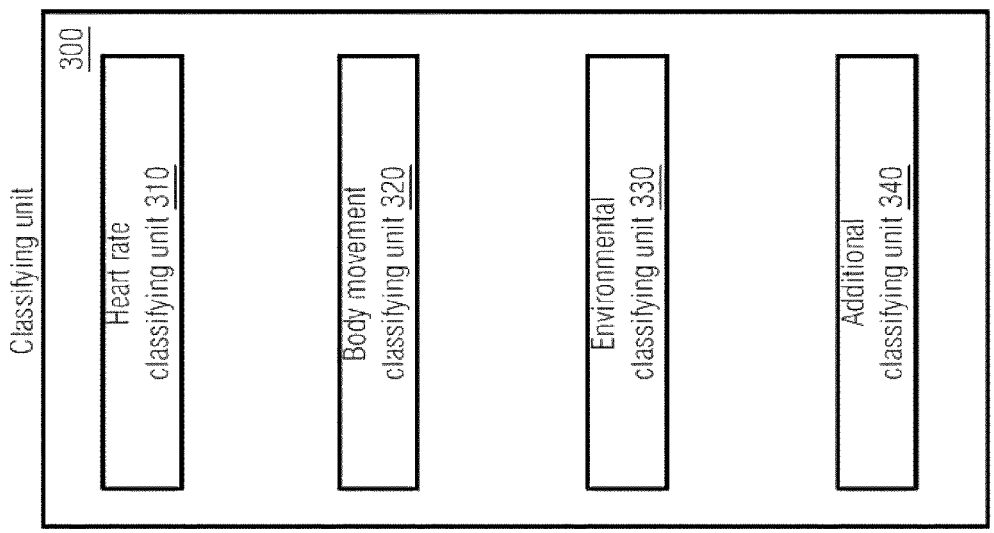
FIG. 3 depicts components of a classifying unit in accordance with an embodiment of the present invention.

According to yet another embodiment, the recording device 100 and data extracting unit 200 are separated into one or more modules. As already stated above, such modules may include all physiological sensors and units (110 to 122), the environmental sensors and units (130 to 150), and the additional sensor 180. In addition, each module will include the corresponding calculating units (210 to 224; 230 to 236; 240) described with respect to data extracting unit 200. FIG. 3 illustrates a block diagram of a classifying unit 300, which may comprise a heart rate classifying means 310, body movement classifying means 320, environmental classifying means 330 and/or additional classifying means 340. Each of the means 310 to 340 can be an entity or unit of classifying unit 300. Such an entity or unit can be a circuitry, such as an integrated circuit (IC), built to perform the functions of the respective means 310 to 340. Alternatively, the entity or unit is a circuit capable of running a specific software or firmware which performs these functions. Preferably and also alternatively, the entity or unit is a processor, such as a microprocessor, executing a conceptual component of a software or firmware, where execution of the conceptual component performs the functions outlined in more detail below.

As one skilled in the art will recognize, the classifying unit 300 may comprise one or all of means or units 310 to 340 depending on the sensors installed in the recording device 100. For instance, if the ambient sensors 130 to 150 are not present in recording device 100, the classifying unit 300 may not need an environmental classifying unit 330.

The classifying unit 300 is capable of accessing the memory where the data outputted by data extracting unit 200 and its sub-units are stored. Therefore, classifying unit 300 provides an interface for wireless or wired data transmissions, such as a network interface, serial or parallel bus interface etc.

The heart rate classifying means 310 classifies the recorded data outputted by heart rate calculating unit 210 either directly from unit 210 or via a memory such as memory 170. This outputted data may include heart rate averages, heart rate variability values, rhythm characteristics and/or heart rate events or changes. Each of these values, if determined by heart rate calculating unit 210, can be classified.

For instance, the HR average may be classified into a high, mid-level and low average. Further, the variability of the heart rate can also be classified into, for example, very high, high, mid-level or low. The classical LF/HF ratio can be obtained from a spectral analysis of heart beat intervals. Other classifications may have a different number of classes, such as 5, 7 or 10 levels. The present invention is not limited to any specific number of classes. The HR classifying means 310 can rather be modified to distinguish between more or less classes, as necessary.

During waking, average heart rate may vary considerably from 60 to 80 beats/minute during resting, to 170 to 190 during a very heavy exercise. The maximum value of heart rate depends on the age of the person and on the prior training. During sleep, average heart rate can be as low as 40 beats/minute. Young adults, physically well trained can reach even lower value during sleep, such as 35 beats/minute. Thus, the classes into which the heart rate classifying means 310 classifies the recorded data may be set differently for the waking state and for the sleeping state. Moreover, the classes can be adjusted to the tested/recorded person based on the age and physical training status of the person.

In addition, the rhythm of the HR can be classified as, for example, very irregular, irregular, regular, and so on. Similarly, the HR events or changes can be classified as acceleration, deceleration or an evoked response. As noted above, the present invention is not limited to these classes, but can include more or less classes. In order to handle future findings, the classes of HR classifying means 310 can be changed, if necessary.

Further, as noted above, the classifying unit 300 can include a body movement (BM) classifying means or unit 320 which can classify the recorded body movement data. Each movement can be classified according to its duration (in seconds) and its intensity (counts per second). As noted above, the number of movements for each second is recorded in the device 100. In case of no movement, the count will be 0 for the considered second.

The BM classifying means 320 derives data output from body movement calculating unit 220, either directly from unit 220 or via a memory, such as memory 170. The BM classifying means 320 may use the intensity of the body movement and/or its duration calculated by BM calculating unit 220. BM classifying means 320 can perform one or more classifications of the body movement. For instance, the BM classifying means 320 is classifying the BM of the tested person into three different classes: large movement (LM), such as posture change, small movement (SM), such as movement of a limb or a hand, and twitches (TM), such as very short movements of the extremities of the body occurring in REM sleep. In addition, the BM intensity can be classified into certain ranges, such as 1 to 2, 3 to 5, and 6 to 10 counts per second. The classes can also be less precise, such as many, limited number, sometimes or a few. Combinations of the two classifications or successive classifications can also be made, such as many movements which often occur continuously, no twitches for a long period or a few isolated small BMs.

Classifying unit 300 can also include environmental classifying means 330 which classifies the recorded environmental factor values of environmental calculating unit 230 and/or subunits 231 to 236. For instance, the calculated noise levels from noise level unit 231 may be classified, for instance, into low level, mid-level or high level noise. Also the noise events determined by noise event unit 232 may be classified by their amplitude, duration, slopes of the rise and decay periods. For instance, a noise event may be classified as very fluctuating, a short but loud noise event or on a low level but for a long period of time.

Environmental classifying means or unit 330 may also classify the average temperature and temperature changes calculated by average temperature unit 233 and temperature change unit 234 respectively. For instance, the average temperature over a particular period of time may be classified as high, mid or low or also as fluctuating. In this case, the environmental classifying means 330 may also take into account the time of day from which the average temperature is calculated. For instance, a particular average temperature may be considered as high during the night while the same average temperature is classified as mid-level during the day. In the same manner, temperature changes may be classified as fluctuating or stable, or as abrupt or long-term changes depending on the duration of the change determined by temperature change unit 234.

Further, the light levels calculated by light level unit 235 can also be classified by environmental classifying means 330 into particular classes such as fluctuating or stable or as bright, dark, etc. Also, the light level changes calculated by the light change unit 236 can also be classified by environmental classifying means 330 into particular classes such as slow change, rapid change, etc. The environmental classifying means 330 may also form classes from two or more values calculated by the units of the environmental calculating means 230, e.g. from units 231 to 236. For instance, the determined light level may be taken into account when classifying the temperature change. For instance, a person leaving a building into hot outside air may be affected by an abrupt change of the temperature as well as an increased light level.

Finally, the additional classifying means or unit 340 may classify data extracted or calculated by additional calculating unit 240 (FIG. 2). For instance, the levels of blood saturation in oxygen may be classified into low, mid and high. Again, other classes and a different number of classes are possible. In addition, in case the pulse transit times (PTTs) were calculated by additional calculating unit 240, the PTTs will also be classified into classes, such as short, medium and long. Depending on the employed additional sensor(s) 180, other classes of data can be derived. Skin temperature will be classified into classes, such as low, medium or high. Similarly, skin electrical potentials will be classified into classes, such as many, moderate or a few.

With respect to heart rate classifying means 310, body movement classifying means 320, environmental classifying means 330 and additional classifying means 340, it is to be noted that the classes into which the particular data is classified may be adjusted by a user. For instance, if particular classes may be of value in the future, the classifying unit 300 can be adapted to also take into account the new classes. On the other hand, existing classes which are of less interest may be removed from the classifying means or units 310 to 340. In addition, any thresholds stored in one of the means 310 to 340 may be modified to adjust the functions of classifying unit 300.

Figure 4:
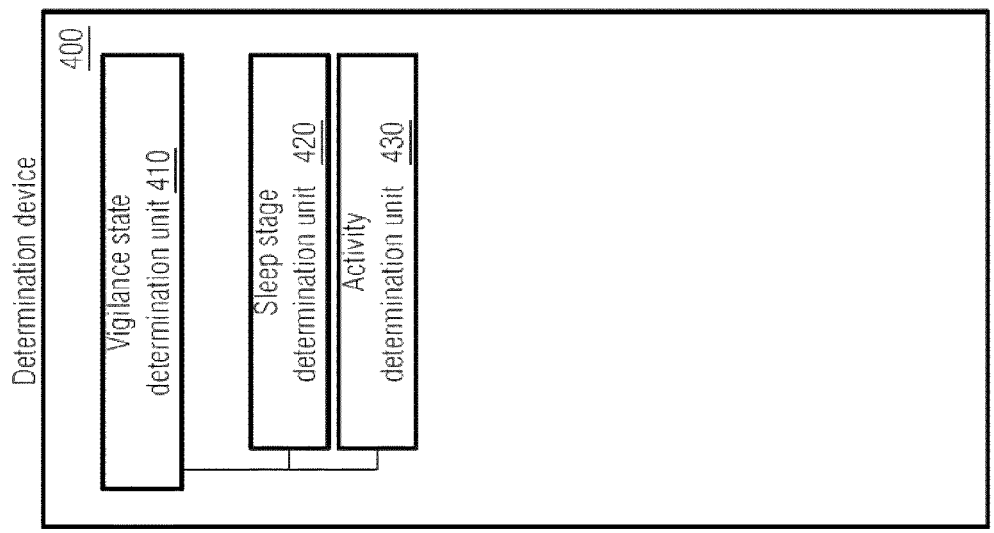
FIG. 4 depicts components of a determination device in accordance with an embodiment of the present invention.

Let us turn to FIG. 4 now, which depicts a determining means 400 for determining a vigilance state, a sleep stage, a sleep stage transition and/or a sleep event of the tested person. The determining means or determination device 400 can include evaluating means 410, such as a vigilance state determination unit 410. The determining means or determination device 400 may further comprise sleep stage determination unit 420 and activity determination unit 430.

The determining means 400 and its sub-means 410 to 430 can each be an entity or unit. Such an entity or unit can be a circuitry, such as an integrated circuit (IC), built to perform the determination and other functions described below. Alternatively, the entity or unit is a circuit capable of running specific software or firmware which performs the functions of the determining means 400 as will be outlined in more detail below. Preferably and also alternatively, the entity or unit is a processor, such as a microprocessor, executing a conceptual component of a software or firmware, where execution of the conceptual component performs these functions.

The evaluating means 410 are optional as the recording device may only be used during sleep periods of the tested/recorded person. If the recording device is worn for a longer period of time including both wakeful periods and sleeping periods, evaluating means 410 evaluates whether the tested person is in a wakefulness period or a sleep period. This evaluation, also referred to as vigilance state determination, can be made by analysing the elaborated data of the classifying unit 300 (FIG. 3), by analysing the data calculated by data extracting unit 200 and/or a combination of the classes and the calculated data. In other words, the classes determined from the sensed and recorded data are taken into account when determining the vigilance state of the tested person. Also the recorded data or a combination of recorded data and classified data may form the basis for further determinations. This may include particularly the heart rate data and/or classes (from unit 210/310) and/or the body movement data and/or classes (from unit 220/320). Additionally, if present, the environmental classes and/or additional classes from units 230/330 and 240/340 can also be used to determine the vigilance state or at least to verify the vigilance state.

The following Table I provides exemplary HR, BM and environmental classes, from which the vigilance state determination unit 410 can determine that the tested person is within a wakeful state or a sleeping state.

TABLE I

| | Class | Wakefulness | Sleep |
|---|---|---|---|
| HR | Average | high | low |
| | Variability | very high | low |
| | Rhythm | very irregular | regular |
| | HR changes or events | many | limited number |
| BM | Large movements | many | a few |
| | Small movements | many, often continuous | not many, isolated |
| | Twitches | not at all | sometimes |
| Environmental | Noise | very fluctuant | seldom events |
| | Temperature | fluctuant | stable |
| | Light | fluctuant | stable |

Basically, large variations in the heart rate and/or the occurrence of numerous movements, in particular large movements, will be present in wakefulness and not during sleep. Also, sudden variations in the ambient physical factors, such as numerous noises, or frequent changes in ambient temperature or ambient light, will be indicative of a moving and therefore awake person.

If it is determined that the vigilance state of the person is a wakeful state, the activity determination unit 430 determines an activity level, such as resting, moderately active or very active. This determination will be based on the number and the sequences of large and small movements, such as numerous by an active person and reduced by a resting one, as well as on the elaborated HR data, such as higher average levels, more HR events or changes, larger HR variability and more irregular rhythm in the very or moderately active than in the resting person. Exemplary HR classes and BM classes of an awake and active person are shown in column "Wake (W)" of Table II below.

If the vigilance state of the tested person has been determined as the sleeping state, sleep stage determination unit 420 distinguishes between different sleep stages and/or identifies sleep events. This distinction and identification can be made based on the heart rate classes identified by unit 310. Further, the distinction and identification can also be based on the body movement classes identified by unit 320 and/or heart rate variability classes.

In addition, sleep stage determination unit 420 can also distinguish between the different sleep stages and can identify sleep stage transitions and/or sleep events by using a cross comparison between the HR and the BM data. The cross comparison can, for example, compare HR classes and BM classes within a temporal relationship. Such temporal relationship may include that the classes are based on data sensed at the same point of time or within the same time period. Moreover, the classes may also be based on HR data sensed before or after sensing the BM data or vice versa. The cross comparison can be made according to certain specific rules and criteria values such as those given exemplary in Table II below.

TABLE II

| | | Wake (W) | Light sleep (LS) | Deep sleep (DS) | REM sleep |
|---|---|---|---|---|---|
| HR | Average | high | W minus 5 to 20 b/min | LS minus 5 to 10 b/min | Between W and LS |
| | Variability | large | small | Very small | large |
| | Rhythm | regular | regular | regular | Very irregular |
| | HR changes or events | many | some | no | Few and brief |
| BM | Large movements | yes | yes | no | no |
| | Small movements | yes | yes | no | no |
| | Twitches | no | no | no | yes |

As shown in Table II, large movements (LM) and small movements (SM) can be seen both during wakefulness and during sleep. However, their number and mainly their succession will be quite different in these two different vigilance states. During wakefulness, LM and SM will be numerous and sometime occurring continuously. This will depend on the activity of the subject and the amount of these motor activities will be used to qualify periods of intense motor activity and periods of low motor activity. During sleep, LM and SM will be infrequent and most of the time separated by long periods of immobility.

Moreover, twitches (TM) will be seen only during sleep and particularly during the REM sleep phases. TM will last for one or two seconds only and the number of counts per second will be low. TM will occur by bursts separated by a few seconds or tens of seconds.

Further, the vigilance state determination unit 410 and the sleep stage determination unit 420 take into account that heart rate and body motility are related as body movement induce an increased need for oxygen delivery to the muscles.

Therefore, any body movement is accompanied by an increased heart rate which is of the type of HRA. A large or sustained BM is accompanied by a larger and sustained increase of HR. The cessation of BM is followed after a variable time by a decrease in HR and a return to its preceding level. The temporal relationship between HR and BM gives a good indication about the current situation.

For instance, if the subject is moving voluntarily, an HRA occurs together with the BM. If the subject is internally aroused (during sleep), an HRA precedes a BM by approximately 6 to 8 heart beats, If the subject is responding to an external stimulus, such as noise, an HRA occurs with or without a BM. When they are associated, a BM might occur within less than the first 5 heart beats of a HRA. If the subject is involuntarily moved by someone else, for example a bed companion, a BM occurs first and then an HRA occurs after a few seconds. In addition, if a pulse oximetry implemented with an additional sensor (see FIG. 2) is present, the above described interrelation of BM and HR can be verified with the classified blood saturation levels of the same time period.

An arousal is a sudden brain activation. It can be associated to an abrupt change from a "deep" stage of NREM sleep to a "lighter" stage of NREM sleep, or from REM sleep to wake, with the possibility of awakening as the final outcome. Arousal may be accompanied by increased heart rate, as well as body movements.

Moreover, although the environmental factors do not need to be recorded, their respective values and combinations can also be used by the vigilance state determination unit 410 and the sleep stage determination unit 420 in order to determine or verify identified sleep stages, sleep stage transitions or sleep events. Noise level, ambient temperature and ambient light might be more or less constant if the subject is staying in the same environment. During sleep, for instance, ambient temperature and ambient light should not be changing much. Their value and their stability will be indicative of quite stable environmental conditions. On the contrary, during the wakefulness period these environmental values will be frequently changing if the subject is moving from one place to another, e.g. going out, using a car etc. Extreme values will even be indicative of severe ambient conditions (very low or very high ambient temperature, high noise level etc.). The effects of these environmental conditions on the HR will be evaluated by the units 410 to 430 of the determination device 400 in order to measure the possible constraints and impact of the physical environment on the subject.

Additionally, sleep stage determination unit 420 can identify a sleep event. The sleep event occurs during sleep spontaneously or in response to external stimuli. For instance, symptoms of sleep pathologies such as sleep apnoea, restless leg, nightmare, night terror, etc. can be identified by specific changes in both heart rate and body movements. In these cases, environmental data such as an ambient noise level is often very valuable. Noise of the final gasp in sleep apnoea and in snoring of a sleeper, or talk and scream in nightmare or night terror are additional signs confirming the physiological changes. A sleep event such as a sudden awakening due to an ambient noise will be identified by both the physiological changes and the preceding noise event. But here too, the main changes are seen in the physiological data and environmental values will be used to confirm or to identify the causal origin of the sleep event.

An example of using information recorded from the additional sensor(s) 180 (FIG. 2) are the pulse transit times (PTTs). If data calculated and classified from these sensors is available, a conclusion can be drawn on the arterial blood pressure of the tested/recorded person during particular time periods. The blood pressure is then used by sleep stage determination unit 420 to determine and/or verify particular sleep stages and/or sleep stage transition and/or sleep events. Thus, a sudden change in blood pressure can be indicative of a sleep disturbance due to an environmental event such as a noise.

A further example of detecting a sleep event involves measuring the blood saturation in oxygen called "pulse oximetry" with an additional sensor 180 (FIG. 2). The measured and classified data of this "pulse oximetry" can be associated with the classified movement data and noise level by sleep stage determination unit 420. If there is a noise detected, e.g. the noise occurring at the end of the apnoea (gasp), the sleep stage determination unit 420 can determine whether there was also a short movement and an associated decrease of the blood saturation in oxygen. If these determinations are positive, this is automatically identified as a sleep event associated with sleep apnoea.

Thus, during sleep, any occurrence of a noise event will be detected and its possible impact on HR and BM will be evaluated. The sleep of the tested person can be disturbed by noise and the consequences might be important in term of sleep structure and sleep fragmentation. Therefore, the impact of nocturnal noise on sleep can be determined.

Further, sudden variations of the ambient temperature cannot be expected when the subject is at rest or sleeping. These changes might occur when the subject is changing places. During sleep, ambient temperature can differ from a neutral condition. It can be too warm in summer or too cold in winter. These conditions can have an impact on sleep and disturb it. If such extreme values are observed, an evaluation of the sleep structure and possible disturbance will be made.

Finally, the level of the ambient light can be different depending on the place the subject is living in. It will also vary depending on the moves of the subject during the day. Its value will be important to determine if the sleeping ambient conditions are those of a low illumination level as expected.

As noted above, the recording device 100 (see FIG. 2) may include an actuator, such as a button, in order to mark particular events by the tested/recorded person. The determination device 400, i.e. unit 410, 420 and/or 430, would then identify the marked events within the recorded data and uses this information when determining the vigilance state, the sleeping stage or a sleep stage transition, and/or a sleep event, respectively. As the marked event may be predefined in the system, the determination device 400 is able to clearly identify associated waking or sleeping states. Moreover, more than one (kind of) event may be marked using different buttons or types of actuation. This may further help the determination device 400 with its tasks. It also allows for training the determination of device 400 or the classification performed by device 300 as is outlined in more detail below.

Figure 8:
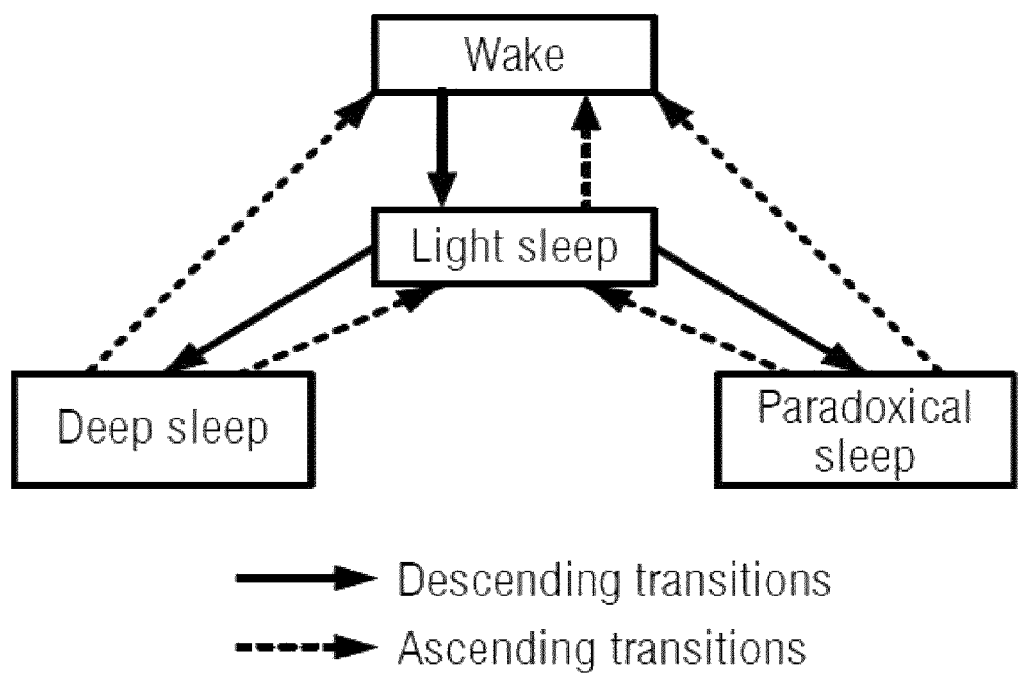
FIG. 8 depicts relations between the vigilance states and sleep stages and illustrates the transitions between these states and stages.

The determination device 400 also determines transitions from one stage to another as they are illustrated in FIG. 8 in a healthy subject. These transitions can also be determined by vigilance state determination unit 410 and/or sleep stage determination unit 420. FIG. 8 depicts a wakefulness state as well as a deep sleep, light sleep and paradoxical sleep (REM) stage. As indicated by the arrows, a transition from one state/stage to another is possible between most of them. However, a transition from wake to deep sleep or from paradoxical sleep to deep sleep will not occur without the intermediate light sleep state.

The transitions from one stage to another can be divided into descending transitions, i.e. those starting from wake or a lighter sleep stage and leading to a deeper one, and ascending transitions, i.e. those going from a deeper sleep stage to a lighter one or to wake. These two types of transitions are preceded and accompanied by specific changes. Exemplary criteria used by the vigilance state determination unit 410 and the sleep stage determination unit 420 for the two types of transitions are given in Table III (descending transitions) and Table IV (ascending transitions) below.

According to a further aspect of the present invention, the determination device 400 is capable of automatically ameliorating itself. As the device has recorded data of several days or weeks at hand it can adjust the determination units according to the behaviour of the tested/recorded person. If a first combination of HR or BM classes and/or data is found which clearly identifies sleep, a specific sleep stage, sleep stage transition or sleep event, the determination device 400 can search for similar combinations which are not as distinctive as the first combination, but are found more often.

TABLE III (descending transitions)

| Descending transitions | Heart rate | Body movement | Remarks |
| --- | --- | --- | --- |
| from Wake to Light sleep | Strong reduction of RHRA; HR becomes regular and less variable; Transition when no HRA for 30 s | BM disappear progressively and transition occurs when no more movement occurs | When awakening occurs; return to LS when HR is back to value prior to awakening |
| from wake to Deep sleep | | | This transition never occurs |
| from wake to REM sleep | Strong reduction of RHRA; Transition when no HRA for 30 s; HR becomes irregular; HRV increases | No BM during the transition but TM might occur | This transition is seen only in narcolepsy when falling asleep; after awakening short LS is often present |
| from Light to Deep sleep | Reduction of RHRA; HR very regular; HRV is very small | No BM is present for several minutes before the transition | The first transition of the night occurs quite quickly; the following ones are longer |
| from Light to REM sleep | HRV increases unexpectedly, while no HRA occurs; HR becomes very irregular | No LM or SM but TM often occur by bursts | This transition is highly predicable due to the strong rhythmicity of REM phase occurrence (see FIG. 1) |
| From REM to Deep sleep | | | This transition never occurs |

TABLE IV (ascending transitions)

| Ascending transitions | Heart rate | Body movement | Remarks |
| --- | --- | --- | --- |
| from Deep sleep to Light sleep or Wake | In most cases there is a HRA accompanied by a LM. If transition to LS: RHRA and HRV are moderately higher than in DS. If transition to W: RHRA and HRV are much higher. | Prior to the transition a LM or posture change occurs accompanied by a large HRA. If transition to LS: BM disappear. If transition to W: BM are present and repeated. | This transition generally occurs after a rather long period of total immobility or after the occurrence of an external event (e.g. loud noise). |
| from Deep sleep to REM sleep | | | This transition is never observed. |
| from REM sleep to Light sleep or Wake | A first HRA is generally accompanied by a BM. If transition to LS: RHRA is about the same but HR is regular and HRV is reduced. If transition to W: RHRA is notably higher and HRA are frequent and associated to BM. | TM disappear and BM is often associated to this transition. The frequency and the intensity of BM will help distinguish between a transition to LS or to W. | In the elderly, REM sleep phases are often terminated by a transition to W. This new stage is often maintained for several minutes. |

Thus, the device 400 can adjust the criteria for sleep, sleep stage, sleep stage transition and sleep event identification.

Moreover, the determination device 400 may also transmit data to the classifying unit 300 in order to configure the classification algorithms. In this manner the classification can be adjusted in order to better identify sleep, sleep stages, sleep stage transitions and/or sleep events.

These techniques may also be used to ameliorate device 400 and unit 300 for better vigilance state detection. Using the recorded data, device 400 may build profiles of the tested person in order to gain average levels, peaks and variations of HR, BM, environmental and/or other sensed data. This may then be used to adjust the classification and determination of unit 300 and device 400 to the daily/nightly behaviour of the tested person. It may also be used to identify the changes induced by a new medical treatment of the tested person or to evaluate if this treatment is leading to amelioration or deterioration of the health status of this person.

Similarly, device 400 can be ameliorated by pooling information obtained from large groups of recorded persons. Thus, the device might better evaluate data from a specific age or sex group. Sleep physiology is quite different in children, young adult or elderly people but inside an age group, the sleep characteristics are quite similar. Therefore, device 400 can integrate collected data in order to better evaluate the normality of the individual recorded data compared to the same age or sex group characteristics.

The determination device 400 may be connected to the classifying unit 300 (FIG. 3) via a data connection to access the different classes output by classifying unit 300. Such a data connection may be implemented as a wireless or wired connection. For instance, a wireless connection may be based on wireless LAN, Bluetooth, infrared data communication or another wireless communication technique. A wired data communication can be implemented with a universal serial bus (USB), Firewire, LAN or another network connection.

The data connections between the described devices and units 100 to 400 may also be used to transfer analysis results to the classifying unit 300, the data extraction unit 200 and/or the recording device 100. Each of these devices may be capable of displaying or otherwise outputting the analysis results. For instance, in case of a wearable device, a display may be integrated where the tested/recorded person can scroll through the analysis results. Further, a printer may be connected to one of the devices 100 to 400 to print the analysis results.

Additionally, the determination device 400 may be capable of sending an analysis report including the results via a network connection. For example, the device 400 may send an email or packet data to a predefined recipient, such as the tested/recorded person or the supervising medical staff or doctor. The determination device 400 may also send or allow access to the recorded raw data (see memory 170 of FIG. 2), the output of data extracting unit 200 and/or the output of the classifying unit 300. A trained person may conduct further analysis of the received or accessed data in order to verify the analysis results or to provide adjustments to the means and units described above with respect to FIGS. 2 to 4. In the case of a recording lasting for several consecutive days or weeks, a description of the significant changes occurring during the long period can be underlined and commented according to the situation. As examples, it can be the case during a medical treatment for a patient or during a training period for an athlete or during a jet-lag period for a travelling person.

According to another embodiment, the classifying unit 300 is part of determination device 400 forming together an analysis device. In this case, a data connection is established between the determination device 400 and data extracting unit 200 (FIG. 2) or a memory such as memory 170, where the extracted data is stored. The data connection can be implemented in the same manner as noted above.

In accordance with yet another embodiment, the devices and units 100, 200, 300 and 400 are combined in one device. In this case, processors and memories of the devices and units can be shared, which reduces the costs of production. Such a combined device can then be connected to a display device or printer to output the determined vigilance states and/or sleep stages over the recording time.

However, the present invention is not restricted to a specific implementation of the different devices and units 100, 200, 300 and 400. It will be noted that any combination of these devices, units and their components falls within the scope of the present invention.

Figure 5:
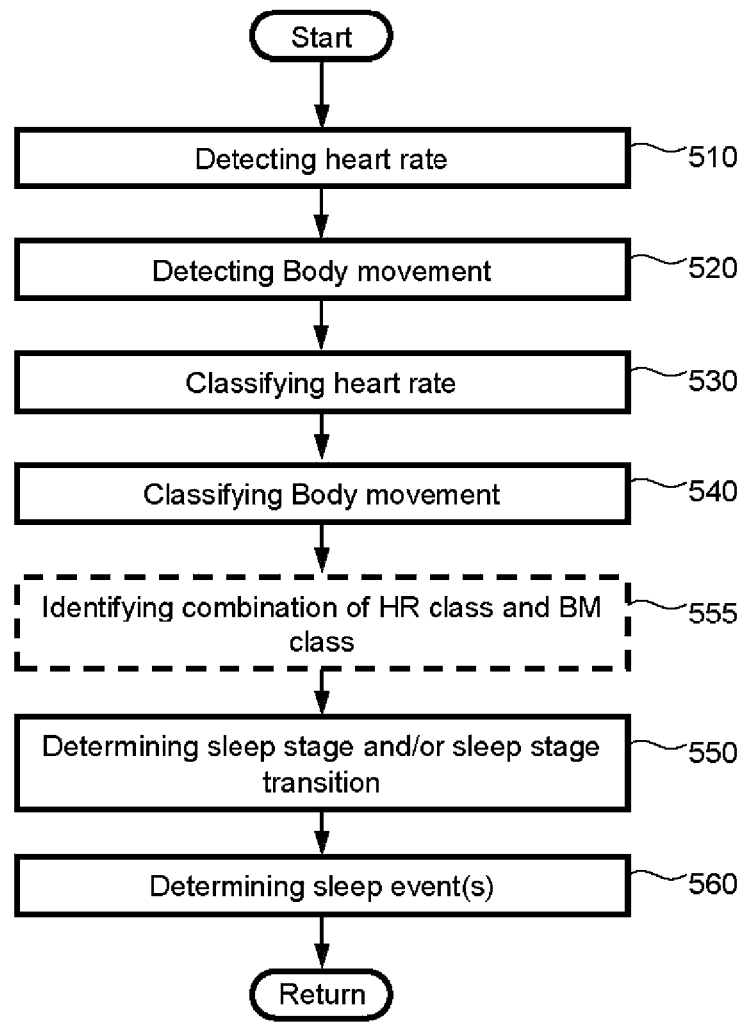
FIG. 5 illustrates method steps of determining sleep, a sleep stage and/or sleep stage transition in accordance with an embodiment of the present invention.

Turning now to FIG. 5, the present invention also defines a method of determining sleep stages, such as that performed by the devices and units described above with respect to FIGS. 2 to 4. The method illustrated in FIG. 5 starts with detecting a heart rate in step 510 from a person to be tested. This detection of the heart rate may be made by a sensor, for example sensing a pulse wave of the tested person and deriving a heart rate there from.

Further, in step 520, a body movement of the tested person is detected. Such detection may be based on an acceleration sensor or other sensor capable of registering a movement of the person. As noted above, the detection of the body movement is focussed on skeletal muscle movement. For instance, an eye movement or movement of any intestines or of the heart of the person are not of interest as a determination of all sleep stages is not possible from these movements alone. A skeletal muscle movement may be a movement of a limb such as arms and legs, the torso or the head of the person. Each of such movements will usually create a movement of the wrist or ankle of the person where the detection of step 520 may take place.

The detected heart rate is then classified in step 530 into particular classes as already outlined above with respect to FIG. 3. A calculation of a heart rate average, heart rate variability, heart rate changes or rhythm characteristics as outlined above with respect to FIG. 2 may precede the classification of the heart rate.

Detected body movements are classified in step 540 as explained above with respect to FIG. 3. Also, a calculation of body movement duration and intensity may precede the classification.

Based on the identified heart rate classes and body movement classes, the sleep stage and/or a sleep stage transition of the person may be determined in step 550. Such determination may be preceded by the determination of a vigilance state. The determination at step 550 is described in more detail above with respect to FIG. 4.

Further, according to step 560 one or more sleep events are detected as also outlined above in regard to FIG. 4.

In addition, in a step 555, a combination of a particular heart rate class and body movement class is identified by performing a cross-comparison. Such identification may be made in relation to a particular period of time. For instance, as outlined above, it is determined whether a particular heart rate class and body movement class from data sensed during the same time or within a close temporal relationship have been determined. Other combinations may be that a particular heart rate class precedes or succeeds a certain body movement class or vice versa.

All of these identified combinations may then be used for the determination of the sleep stage in step 550. Exemplary combinations are shown above in Table I.

Figure 6:
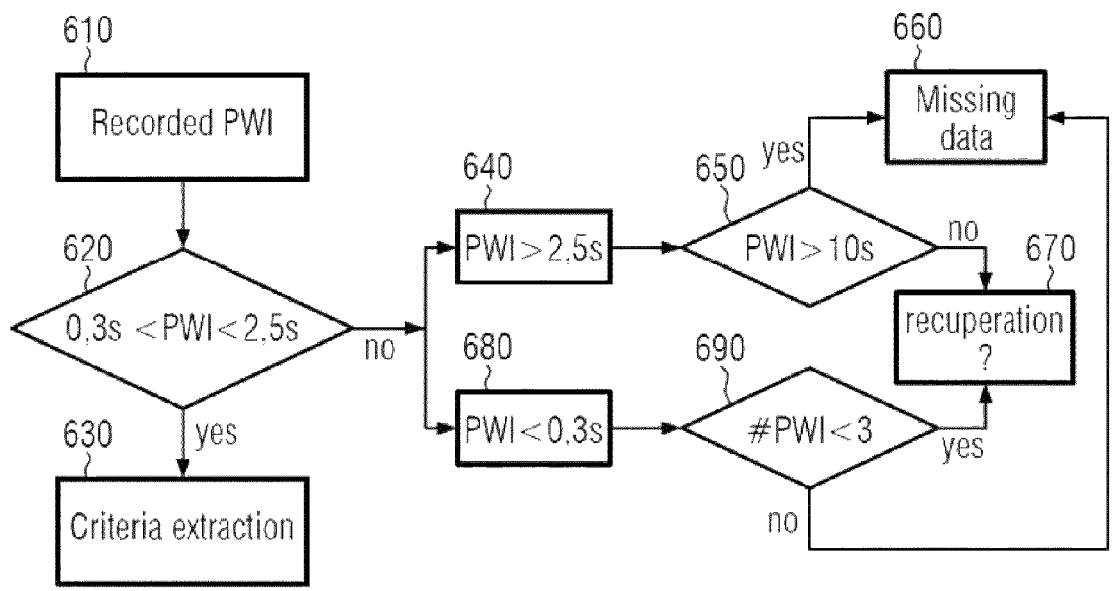
FIG. 6 illustrates method steps of the verification of a heart rate recording in accordance with another embodiment of the present invention.

Turning to FIG. 6, in order to improve the classification of the HR data, the present invention also provides for recuperation of missing or abnormal pulse wave interval (PWI) data. For instance, heart rate calculating unit 210 (FIG. 2) may perform the steps described with respect to FIG. 6.

In detail, as also explained above, successive pulse wave intervals (PWI) are recorded in a step 610 to then retrieve the instantaneous heart rate. The PWIs of more than 2500 msec (milliseconds) correspond to instantaneous heart rate of less than 24 beats/minute (b/min). Such PWIs are considered as missing PWI data. In addition, intervals shorter than 300 msec correspond to an instantaneous heart rate of more than 200 beats/minute and are considered as suspicious PWIs. Therefore a determination is made in step 620 whether a recorded PWI falls within the range of 300 msec to 2500 msec (0.3 s to 2.5 s).

If the PWI falls within this range (step 630), the PWI is considered as correct and can be used for further calculations or classification of the HR data.

If the PWI does not fall within this range, the method proceeds at step 640 in case the PWI is greater than 2500 msec. It is then determined in step 650 whether the PWI is longer than 10 seconds. If yes, this interval is considered as corresponding to missing data (step 660).

If the PWI is shorter than 300 msec (step 680), the method proceeds at step 690, determining whether the number of PWIs shorter than 300 msec is less than 3. If the number of such short PWIs is greater than or equal 3, these intervals are also considered as corresponding to missing data.

Missing data will not be recuperated as they will correspond to a technical problem in the recording process. If the only missing data concern pulse wave recording, it will be caused by failure in the pulse detection system or by an incorrect placement of the recording device. If the missing data concern all recording channels, this will be due to a memory or a battery failure.

Missing PWI and suspicious PWI will be due to a momentary stop of the recording or to an artefact produced by displacement of the recording device. Under certain conditions, missing PWI (2.5 s<PWI<10 s) and suspicious PWI (PWI<0.3 s and #PWI<3) can be recuperated in step 670. In order to do so, it is first verified that at least 10 PWI preceding the missing PWI or the suspicious PWI and that at least 10 PWI following them are in the normal range (0.3 s<PWI<2.5 s). If so, the missing PWI or the suspicious PWI are replaced by the average value of the 10 normal PWI preceding and the 10 normal PWI following them.

The present invention utilizes the fact that changes in sleep stages are accompanied by changes in the vegetative (heart rate) and motor (movements) functions. Considering these two variables and their temporal relationships, our invention allows not only to distinguish these stages but also to determine very precisely the time when sleep stage transitions do occur. A few and specific examples of such transitions are given in FIGS. 10 to 13.

Figure 10:
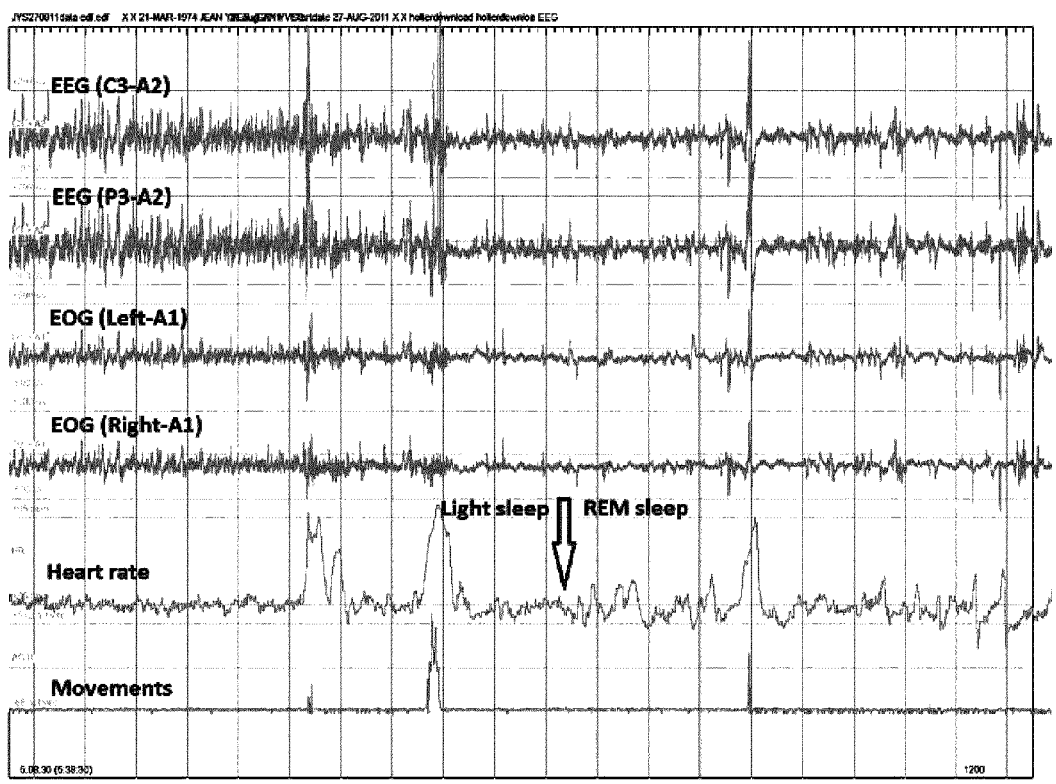
FIG. 10 illustrates a sleep stage transition from light sleep to REM sleep.

For instance, FIG. 10 shows a transition from light sleep to REM sleep. This figure represents a 20-minute period recording. On the upper part of it are registered two electroencephalograms (EEG) and two electrooculograms (EOG). The vertical arrow indicates the exact transition from light sleep to REM sleep as determined using conventional sleep stage scoring by analysing visually the upper four traces.

The lower part of the figure shows recordings of a short-time heart rate average (measuring time is approximately 5 seconds) and body movements. The left half of the figure shows that the variability of heart rate is small in light sleep except when the sleeper is moving. The two movements occurring in light sleep are accompanied by large increases in heart rate (heart rate change of about 20 beats). The right half of the figure shows that in REM sleep, heart rate variability is large and that the numerous heart rate changes seen (except the largest one) are not accompanied by movements. Thus this sudden change in the relationship between heart rate and body movements is specific of the transition from light sleep to REM sleep (see also table III).

Figure 11:
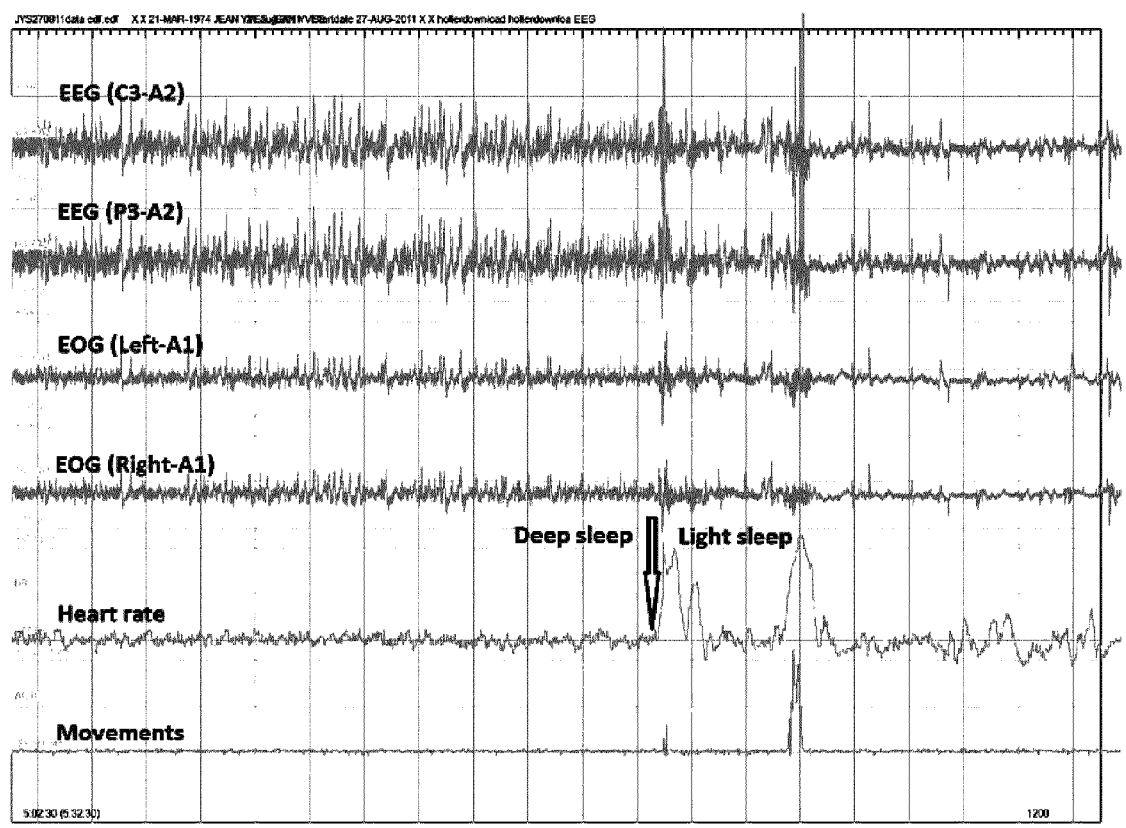
FIG. 11 illustrates a sleep stage transition from deep sleep to light sleep.

FIG. 11 presents a transition from deep sleep to light sleep. Here again, a 20-minute period is considered. The same traces as in FIG. 10 are present here. The exact transition from deep sleep to light sleep, as determined by visual analysis of EEGs and EOGs, is indicated by a vertical arrow. In the left part of the figure we see that heart rate variability is very small in deep sleep and that no body movement are present during this sleep stage (see also tables II and IV). The transition to light sleep is accompanied by two movements inducing large heart rate changes. Later on, heart rate variability is larger than in deep sleep.

Figure 12:
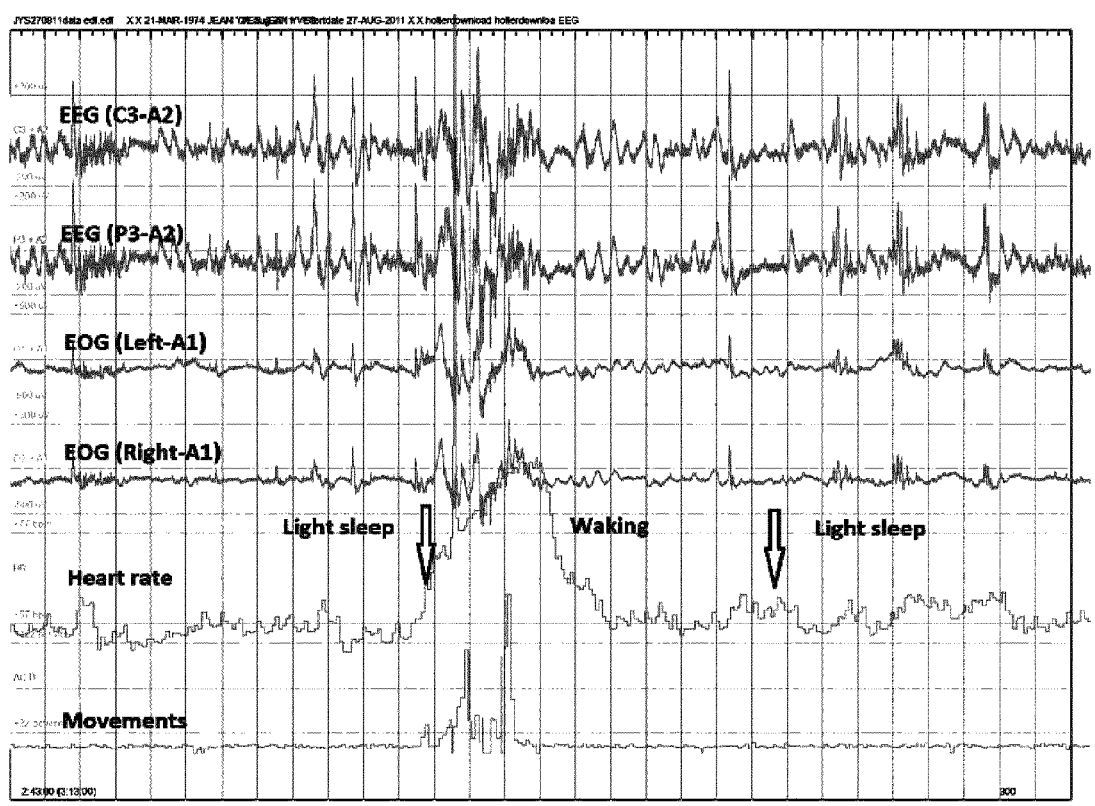
FIG. 12 illustrates a short transition from light sleep to waking followed by a return to light sleep.

In FIG. 12 are represented a short transition from light sleep to waking and a return to light sleep. This time, due to the short duration of the nocturnal awakening, the length of the recording is of 5 minutes only. The two transitions are marked by vertical lines. Here, the waking episode is lasting 1 minute and 40 seconds only (distance between two grey vertical lines corresponds to 10 seconds). The transition from light sleep to waking is accompanied by a large and long body movement (about 30 seconds) and heart rate is increased very much. Immediately after the movement, heart rate keeps a higher value than in previous light sleep, signing the waking state of the subject (see also table IV). The return to a much lower heart rate value, comparable to the one seen before the waking episode is followed by the transition from waking to light sleep.

Figure 13:
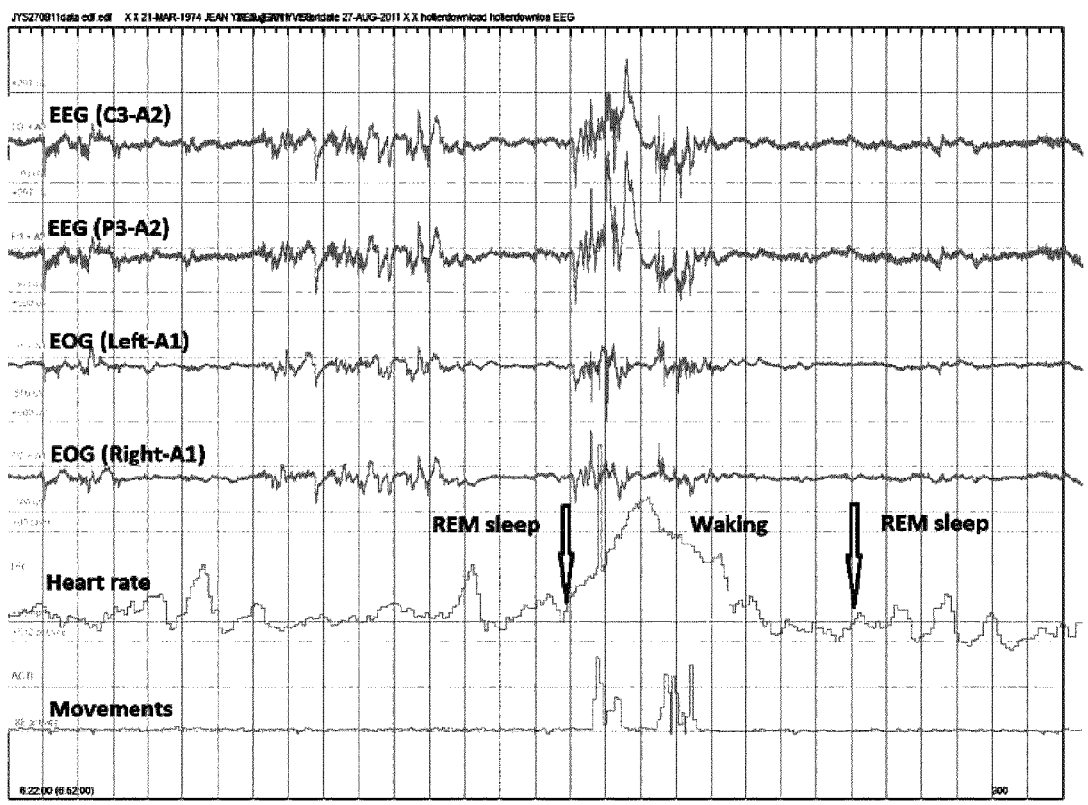
FIG. 13 illustrates a short transition from REM sleep to waking followed by a return to REM sleep.

FIG. 13 shows a short transition from REM sleep to waking and a return to the stage of REM sleep afterwards. Here also, for a better comprehension of the changing features, the recording time is only of 5 minutes and the duration of the waking episode is only 1 minute and 10 seconds long. On the left hand part of the figure, REM sleep is characterized by highly fluctuating heart rate where changes are not due to body movements but to very irregular heartbeats (see also table II). The waking episode is accompanied by a massive increase in heart rate accompanied by a large body movement lasting about 30 seconds. After a return to a heart rate value comparable to the one seen before the awakening, subject returns to REM sleep and its characteristic fluctuating heart rate not related to body movements.

These few examples demonstrate that sleep stages, sleep stage transitions and/or sleep events can be determined by analyzing the heart rate and body movements and their temporal relationships. As described above, this analysis can be made by defining parameters such as heart rate average, heart rate variability, body movement, etc. and by classifying each of these parameters into at least one class. Together with the criteria defining the established sleep stages indicated above, these data permit to precisely determine sleep, sleep stages, and/or sleep stage transitions. This complementary approach is the only way to obtain an objective hypnogram equivalent to the one derived from the visual analysis of the polysomnography.

The present invention allows for recording, calculating and classifying physiological and/or environmental data in order to produce a global report on the sleep structure and sleep quality after the exploitation of the recorded and classified data. The report will include statistic data such as time awake, resting time, time in bed, time asleep, sleep efficiency, time to fall asleep, time and percent of time spent in the different stages of sleep, number of sleep stage changes, number of movements, number of awakenings, etc. The sleep structure of one given night will be compared to previous records of the same individual if desired. This could be done in order to evaluate a change in the sleep structure and quality due to a change in the living environment or to evaluate the effects of a pharmacological treatment or to follow the sleep modifications due to a jet-lag, etc.

Another advantage of the present invention is that the recording of the ambient physical factors will help in the evaluation of sleep disturbance related to the possible variations of these factors during the sleep period. Ambient noise can disturb sleep and the reduced sleep length is due to possible delayed time to fall asleep, nocturnal awakenings and early final awakening. In some cases, noise does not awake the sleeping person but it produces arousals, sleep stage changes, and cardiovascular modifications. Ambient temperature can also have a strong effect on sleep structure and quality. Thus, high or low ambient temperature will be accompanied by numerous awakenings, reduced amount of deep and REM sleep stages together with an increase in body motility. Such a disturbance can explain the daily fatigue experienced by the poor sleeper, although non-consciously related to the nocturnal environment. All these effects are detected by the system and method of the present invention. The final report on the sleep structure and sleep quality may include specific information on the environmental factors which might be disturbing the sleeper.

Further, the existence of abnormal events occurring during sleep or of sleep pathologies is often ignored by the general population. The system of the present invention can detect some of these events and pathologies by using the information coming from the biological variables and/or the information coming from the ambient factors recorded by the device.

For example, snoring and its often associated obstructive sleep apnoea syndrome will be detected by the variations in heart rate and the occurring body movement at the end of the apnoea, but also from the noise recording detecting the snore and the final gasp. Specific measures of oximetry (blood level of oxygen saturation) and of arterial pressure could easily be associated to specific recordings of the present invention in order to evaluate the severity of the symptoms. Sleep events, such as abnormal movement, for example the restless leg syndrome, can be detected by the accelerometer. Sleepwalking can be detected by the above modifications and the simultaneous changes in the ambient parameters. Abnormal sleep lengths such as insomnia or hypersomnia can be measured and quantified. Narcolepsy can be detected by the sudden short sleep episodes occurring during waking and also by the REM sleep onset or advanced first REM sleep phase. Other sleep events such as sleep terror crises and nightmares can also be detected by the combination of biological and physical measures. Finally, the system can also be very valuable in the field of neuro-psychiatric disorders. Indeed, several observations suggest important links between sleep and mental disorders. For neuropsychiatric disorders the link is the most evident, such as for major mood disorders, such as depression, schizophrenia, degenerative disorders of ageing, and Parkinson's disease. For most of these diseases mentioned above sleep is a good bio marker contributing to a better diagnostic as well as to a more accurate evaluation and quantification of the therapeutic effect of either pharmacological or psychological treatments. Interestingly enough it becomes more and more clear also that some of the cognitive disturbances observed in these pathologies are strongly improved if sleep is improved or normalized.

From a chronobiological point of view, the continuous recording made by the present invention over several days or weeks will also allow evaluating the normality of the basic circadian and ultradian rhythms of the person. In several pathologies, these rhythms are profoundly disturbed and their return to normal might be highly indicative of the clinical evolution of the illness or the efficacy of a given treatment.

The invention claimed is:

1. A system for determining sleep, a sleep stage, sleep stage transition, and/or a sleep event of a person, comprising:
   a wearable device configured for detecting and recording a heart rate of the person and configured for detecting and recording a movement of a part of the body of the person, wherein the movement is caused by a skeletal muscle of the body;
   an analysis device configured for classifying the recorded heart rate of the person into at least one heart rate class and at least one heart rate variability class, configured for classifying the recorded movement into a movement class comprising a large movement (LM), a small movement (SM) or a twitch (TM), based on a calculated intensity and/or duration of each movement, wherein the analysis device is capable of classifying the movement into any of the LM, SM, and TM, and configured for determining sleep, a sleep stage, a sleep stage transition and/or a sleep event of the person based at least partially on the at least one heart rate class, the at least one heart rate variability class, and the movement class; and
   a data connection configured for communicating data representing the recorded heart rate and the recorded movement from the wearable recording device to the analysis device, and wherein the analysis device is configured for classifying the recorded movement into the movement class based on the calculated intensity level of 1 to 2 counts per second, 3 to 5 counts per second, or 6 to 10 counts per second.

2. A system for determining sleep, a sleep stage, sleep stage transition, and/or a sleep event of a person, the system comprising:
   heart rate detecting means configured for detecting a heart rate of the person;
   movement detecting means configured for detecting a movement of a part of the body of the person caused by a skeletal muscle of the body and comprising movement sensing means configured for sensing an acceleration of the part of the body;
   recording means configured for recording the detected heart rate and the detected movement of the part of the body;

movement calculating means configured for calculating, based on values of the sensed acceleration, at least an intensity and/or a duration of each movement of the part of the body;

heart rate classifying means configured for classifying the recorded heart rate of the person into at least one heart rate class and at least one heart rate variability class;

movement classifying means configured for classifying the recorded movement into a movement class comprising a large movement (LM), a small movement (SM), or a twitch movement (TM), based on the calculated intensity and/or the calculated duration of each movement, wherein the movement classifying means is capable of classifying the movement into any of the LM, SM, and TM; and determining means configured for determining sleep, a sleep stage, a sleep stage transition and/or a sleep event of the person based at least partially on the at least one heart rate class, the at least one heart rate variability class, and the at movement class, and wherein the movement classifying means are configured for classifying the recorded movement into the movement class based on the calculated intensity level of 1 to 2 counts per second, 3 to 5 counts per second, or 6 to 10 counts per second.

3. The system according to claim 2, further comprising:
heart rate calculating means configured for calculating a heart rate average, a variability value, a rhythm characteristic and/or a heart rate event or change from the recorded heart rate, wherein the heart rate classifying means are configured for classifying the heart rate of the person based on the calculated heart rate average, variability value, rhythm characteristic and/or heart rate event or change from the recorded heart rate.

4. The system according to claim 2, wherein the determining means are further configured for identifying a specific combination of a heart rate class, a heart rate variability class, and a movement class within a specific time period, and wherein the determining means are configured for determining sleep, the sleep stage, a sleep stage transition and/or a sleep event based on the identified specific combination.

5. The system according to claim 2, wherein the movement classifying means are further configured for classifying each LM, SM and/or TM at least into frequency classes and/or duration classes.

6. The system according to claim 2, further comprising:
environmental sensing means configured for sensing at least one environmental factor, wherein the recording means are further configured for recording the sensed at least one environmental factor; and environmental classifying means configured for classifying at least some values of the at least one recorded environmental factor into at least one environmental class, wherein the determining means are further configured for determining sleep, the sleep stage, the sleep stage transition and/or the sleep event of the person based at least partially on the at least one environmental class.

7. The system according to claim 6, wherein the environmental sensing means are configured for sensing a noise level, an ambient temperature and/or an ambient light, the system further comprising:

environmental calculating means configured for calculating at least one average noise level and/or noise change and/or noise event based on the recorded noise level, and/or calculating at least one average ambient temperature level and/or change and/or variation based on the recorded ambient temperature, and/or calculating at least one ambient light level and/or change of ambient light level based on the recorded ambient light.

8. The system according to claim 6, wherein the determining means are further configured for determining a transition from waking to sleeping and/or a transition from one sleep stage to another and/or a transition from sleeping to waking and/or a direct causal effect of at least one recorded environmental factor on a sleep stage transition or a transition from sleeping to waking.

9. The system according to claim 6, further comprising: evaluating means configured for evaluating a sleeping or waking state of the person based on the at least one heart rate class, the at least one heart rate variability class, and the at movement class, the at least one environmental class and/or any combination thereof.

10. The system of claim 2, wherein the at least one heart rate class comprises a heart rate average class.

11. The system according to claim 2, wherein the determining means are configured for identifying a combination of a heart rate class, a heart rate variability class, and a movement class within a time period, and for determining sleep, a sleep stage, a sleep stage transition, and/or a sleep event based on the identified combination.

12. A method for determining sleep, a sleep stage, a sleep stage transition, and/or a sleep event of a person, the method comprising:
detecting a heart rate of the person;
recording the detected heart rate;
detecting a movement of a part of the body of the person, wherein the movement is caused by a skeletal muscle of the body;
recording the detected movement;
classifying the recorded heart rate of the person into at least one heart rate class and at least one heart rate variability class;
classifying the recorded movement into a movement class comprising a large movement (LM), a small movement (SM), or a twitch movement (TM), based on a calculated intensity and/or the calculated duration of each movement, wherein the classifying includes classifying the movement into any of the LM, SM, and TM; and
determining sleep, a sleep stage, a sleep stage transition and/or a sleep event of the person based at least partially on the at least one heart rate class, the at least one heart rate variability class, and the movement class, and wherein classifying the recorded movement into the movement class is based on the calculated intensity level of 1 to 2 counts per second, 3 to 5 counts per second, or 6 to 10 counts per second.

13. The method according to claim 12, the method comprising: identifying a specific combination of a heart rate class, a heart rate variability class and a movement class within a specific time period, and wherein determining comprises determining sleep, a sleep stage, a sleep stage transition, and/or a sleep event based on the identified specific combination.

14. The method according to claim 12, the method further comprising:
sensing at least one environmental factor;
recording the sensed at least one environmental factor;
classifying at least some values of the at least one recorded environmental factor into at least one environmental class; and determining a sleeping or waking state of the person based at least partially on the at least one environmental class.

15. The method according to claim 14, the method further comprising: determining a direct causal effect of at least one recorded environmental factor on a sleep stage transition or a transition from sleeping to waking based at least partially on the at least one environmental class.

* * * * *